United States Patent [19]
Kovelman et al.

[11] Patent Number: 5,820,602
[45] Date of Patent: Oct. 13, 1998

[54] PEN-TYPE INJECTOR DRIVE MECHANISM

[75] Inventors: Paul H. Kovelman, Simi Valley, Calif.; Thomas P. Castellano, Reno, Nev.

[73] Assignee: Visionary Medical Products, Inc., Beverly Hills, Calif.

[21] Appl. No.: 706,609

[22] Filed: Sep. 5, 1996

[51] Int. Cl.⁶ .................................................. A61M 5/00
[52] U.S. Cl. .......................................... 604/187; 604/156
[58] Field of Search ................................. 604/187, 208, 604/207, 218, 232, 224, 234, 228, 156

[56] References Cited

U.S. PATENT DOCUMENTS

| | | |
|---|---|---|
| 1,997,129 | 4/1935 | Taylor et al. . |
| 2,221,739 | 11/1940 | Reiter . |
| 2,605,763 | 8/1952 | Smoot . |
| 2,632,445 | 3/1953 | Kas . |
| 2,695,023 | 11/1954 | Brown . |

(List continued on next page.)

FOREIGN PATENT DOCUMENTS

| | | |
|---|---|---|
| 55604/86 | 10/1987 | Australia . |
| 1103314 | 6/1981 | Canada . |
| 0037696 | 10/1981 | European Pat. Off. . |
| 0058536 | 8/1982 | European Pat. Off. . |
| 0143895 | 6/1985 | European Pat. Off. . |
| 0368191 | 11/1988 | European Pat. Off. . |
| 0327910 | 1/1989 | European Pat. Off. . |
| 0416975 | 3/1991 | European Pat. Off. . |
| 91225137 | 7/1991 | European Pat. Off. . |
| 93249687 | 7/1993 | European Pat. Off. . |
| 1149735 | 12/1957 | France . |
| 1170312 | 1/1959 | France . |
| 1445659 | 12/1966 | France . |
| 2418642 | 9/1979 | France . |
| 2557445 | 5/1985 | France . |
| 730971 | 12/1942 | Germany . |

(List continued on next page.)

OTHER PUBLICATIONS

PCT Written Opinion issued by the European Patent Office on Nov. 3, 1995.
Search Report for PCT/US95/02727, mailed Jun. 20, 1995.
Annual International Conference of the IEEE Engineering in Medicine and Biology Society, "An Optical and RF Telemetry Drug Injection Control and ECG System for Awake Small Animal Studies", vol. 13, No. 5, 1991.
PCT International Search Report, Jan. 20, 1997.

Primary Examiner—Michael Buiz
Assistant Examiner—Kevin Truong
Attorney, Agent, or Firm—Pillsbury Madison & Sutro LLP

[57] ABSTRACT

A medication injection mechanism, for delivering a dosage of medication from a medication cartridge having a piston, includes a two-piece drive shaft, a rachet mechanism, and a drive mechanism. The two-piece drive shaft includes a plunger portion and a drive portion. The plunger portion has an end that contacts the piston of the medication cartridge, ratchet teeth disposed on the sides of the plunger portion that define a thickness of the plunger portion, and an opening to provide a passage through the plunger portion of the two-piece drive shaft. The drive portion is formed by rails that are coupled together by a connector that passes through the opening in the plunger portion so that the drive portion is coupled to the plunger portion, and can move relative to the plunger portion. Each of the rails forming the drive portion has threads on a surface that extend beyond the defined thickness of the plunger portion. The ratchet mechanism engages with the ratchet teeth of the plunger portion to permit the movement of the plunger portion toward the piston of the medication cartridge and to inhibit movement of the plunger portion away from the piston of the medication cartridge. Also, the drive mechanism engages with the threads on the rails of the drive portion, but is free of contact with the ratchet teeth on the plunger portion to adjust the position of the drive portion relative to the plunger portion so that the drive portion can be moved toward the piston of the medication cartridge a fixed distance and the plunger portion is moved a distance that is less than or equal to the fixed distance.

14 Claims, 30 Drawing Sheets

U.S. PATENT DOCUMENTS

| | | |
|---|---|---|
| 2,718,299 | 9/1955 | Atwater et al. . |
| 3,110,310 | 11/1963 | Cislak . |
| 3,141,583 | 7/1964 | Mapel et al. . |
| 3,293,749 | 12/1966 | George et al. . |
| 3,348,545 | 10/1967 | Sarnoff et al. . |
| 3,481,510 | 12/1969 | Allen, Jr. . |
| 3,517,668 | 6/1970 | Brickson . |
| 3,583,399 | 6/1971 | Ritsky . |
| 3,894,663 | 7/1975 | Carhart et al. . |
| 3,977,574 | 8/1976 | Thomas . |
| 4,022,207 | 5/1977 | Citrin . |
| 4,099,548 | 7/1978 | Sturm et al. . |
| 4,114,619 | 9/1978 | Wagner . |
| 4,139,008 | 2/1979 | Wagner . |
| 4,146,029 | 3/1979 | Ellinwood, Jr. . |
| 4,169,474 | 10/1979 | Wagner . |
| 4,284,077 | 8/1981 | Wagner . |
| 4,333,458 | 6/1982 | Margulies et al. . |
| 4,393,870 | 7/1983 | Wagner . |
| 4,395,921 | 8/1983 | Oppenlander . |
| 4,413,760 | 11/1983 | Paton . |
| 4,415,101 | 11/1983 | Shapiro et al. . |
| 4,425,121 | 1/1984 | Young et al. . |
| 4,435,173 | 3/1984 | Siposs et al. . |
| 4,444,560 | 4/1984 | Jacklich . |
| 4,457,712 | 7/1984 | Dragan . |
| 4,470,317 | 9/1984 | Sabloewski et al. . |
| 4,475,905 | 10/1984 | Himmelstrup . |
| 4,498,904 | 2/1985 | Turner et al. . |
| 4,509,905 | 4/1985 | Michel . |
| 4,526,294 | 7/1985 | Hirschmann et al. . |
| 4,529,401 | 7/1985 | Leslie et al. . |
| 4,538,616 | 9/1985 | Rogoff . |
| 4,573,970 | 3/1986 | Wagner . |
| 4,581,022 | 4/1986 | Leonard et al. . |
| 4,592,745 | 6/1986 | Rex et al. . |
| 4,600,403 | 7/1986 | Wagner . |
| 4,613,328 | 9/1986 | Boyd . |
| 4,659,327 | 4/1987 | Bennett et al. . |
| 4,664,128 | 5/1987 | Lee . |
| 4,710,172 | 12/1987 | Jacklich et al. . |
| 4,710,178 | 12/1987 | Leonard et al. . |
| 4,820,287 | 4/1989 | Leonard . |
| 4,865,591 | 9/1989 | Sams . |
| 4,883,472 | 11/1989 | Michel . |
| 4,936,833 | 6/1990 | Sams . |
| 4,950,246 | 8/1990 | Muller . |
| 4,959,056 | 9/1990 | Dombrowski et al. . |
| 4,998,570 | 3/1991 | Strong . |
| 5,024,656 | 6/1991 | Gasaway et al. . |
| 5,047,044 | 9/1991 | Smith et al. . |
| 5,050,612 | 9/1991 | Matsumura . |
| 5,069,668 | 12/1991 | Boydman . |
| 5,085,642 | 2/1992 | Sarnoff et al. . |
| 5,092,842 | 3/1992 | Bechtold et al. . |
| 5,102,393 | 4/1992 | Sarnoff et al. . |
| 5,104,380 | 4/1992 | Holman et al. . |
| 5,112,317 | 5/1992 | Michel . |
| 5,114,406 | 5/1992 | Gabriel et al. . |
| 5,139,484 | 8/1992 | Hazon et al. . |
| 5,180,371 | 1/1993 | Spinello . |
| 5,226,895 | 7/1993 | Harris . |
| 5,226,896 | 7/1993 | Harris . |
| 5,244,461 | 9/1993 | Derlien . |
| 5,244,465 | 9/1993 | Michel . |
| 5,249,584 | 10/1993 | Karkar et al. . |
| 5,256,157 | 10/1993 | Samiotes et al. . |
| 5,279,294 | 1/1994 | Anderson et al. . |
| 5,279,585 | 1/1994 | Balkwill . |
| 5,279,586 | 1/1994 | Balkwill . |
| 5,383,865 | 1/1995 | Michel . |
| 5,425,716 | 6/1995 | Kawasaki et al. . |
| 5,429,602 | 7/1995 | Hauser . |
| 5,540,664 | 7/1996 | Wyrick ................................. 604/208 |
| 5,593,390 | 1/1997 | Castellano et al. .................. 604/187 |

FOREIGN PATENT DOCUMENTS

| | | |
|---|---|---|
| 1070784 | 12/1959 | Germany . |
| 22140 | 10/1961 | Germany . |
| 293302 | 9/1953 | Switzerland . |
| 1225495 | 3/1971 | United Kingdom . |
| 1574267 | 9/1980 | United Kingdom . |
| 2109690 | 2/1982 | United Kingdom . |
| WO8502546 | 6/1985 | WIPO . |
| 8601728 | 3/1986 | WIPO . |
| 9213583 | 8/1992 | WIPO . |
| WO9310838 | 6/1993 | WIPO . |
| WO95/24233 | 9/1995 | WIPO . |

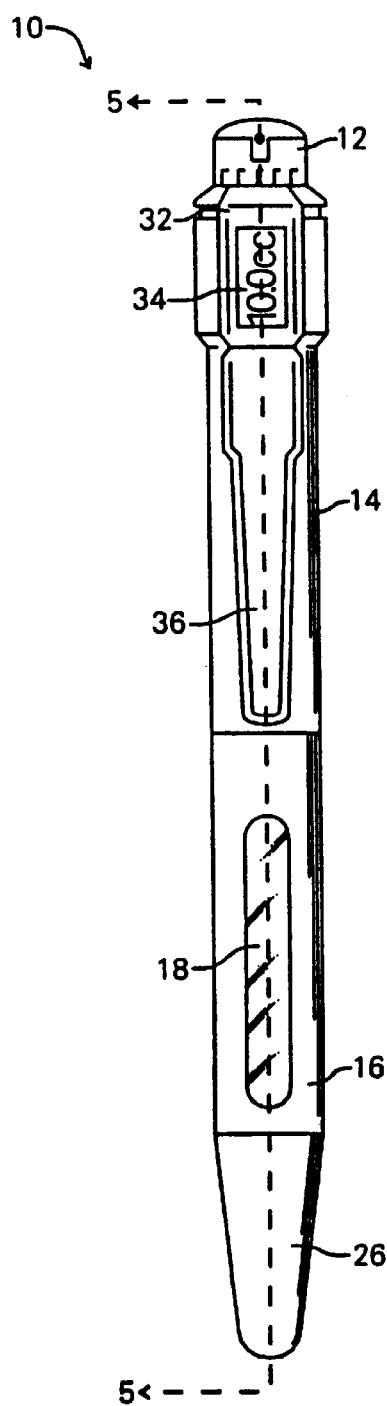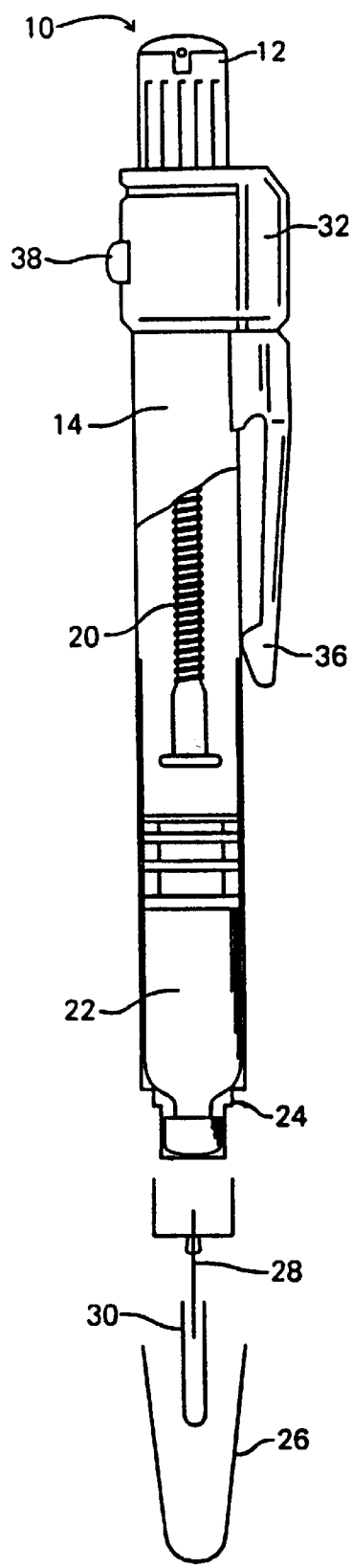
FIG. 2
FIG. 3

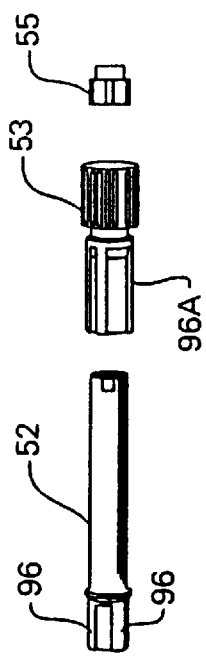
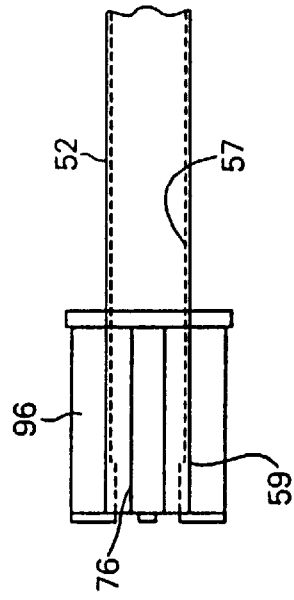
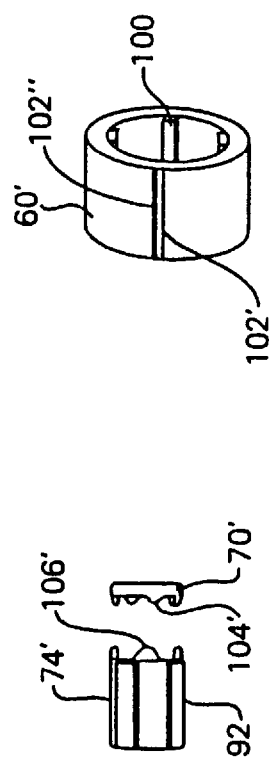
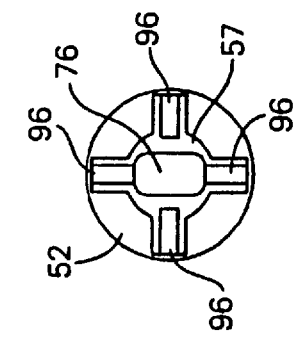
FIG. 7(d)
FIG. 7(f)
FIG. 7(c)
FIG. 7(b)
FIG. 7(e)

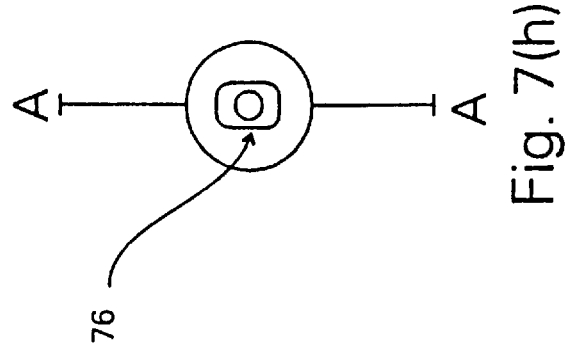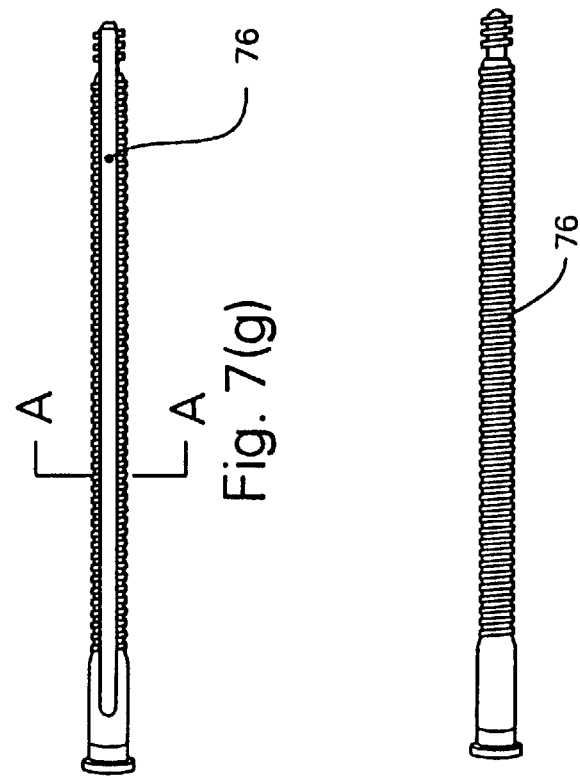

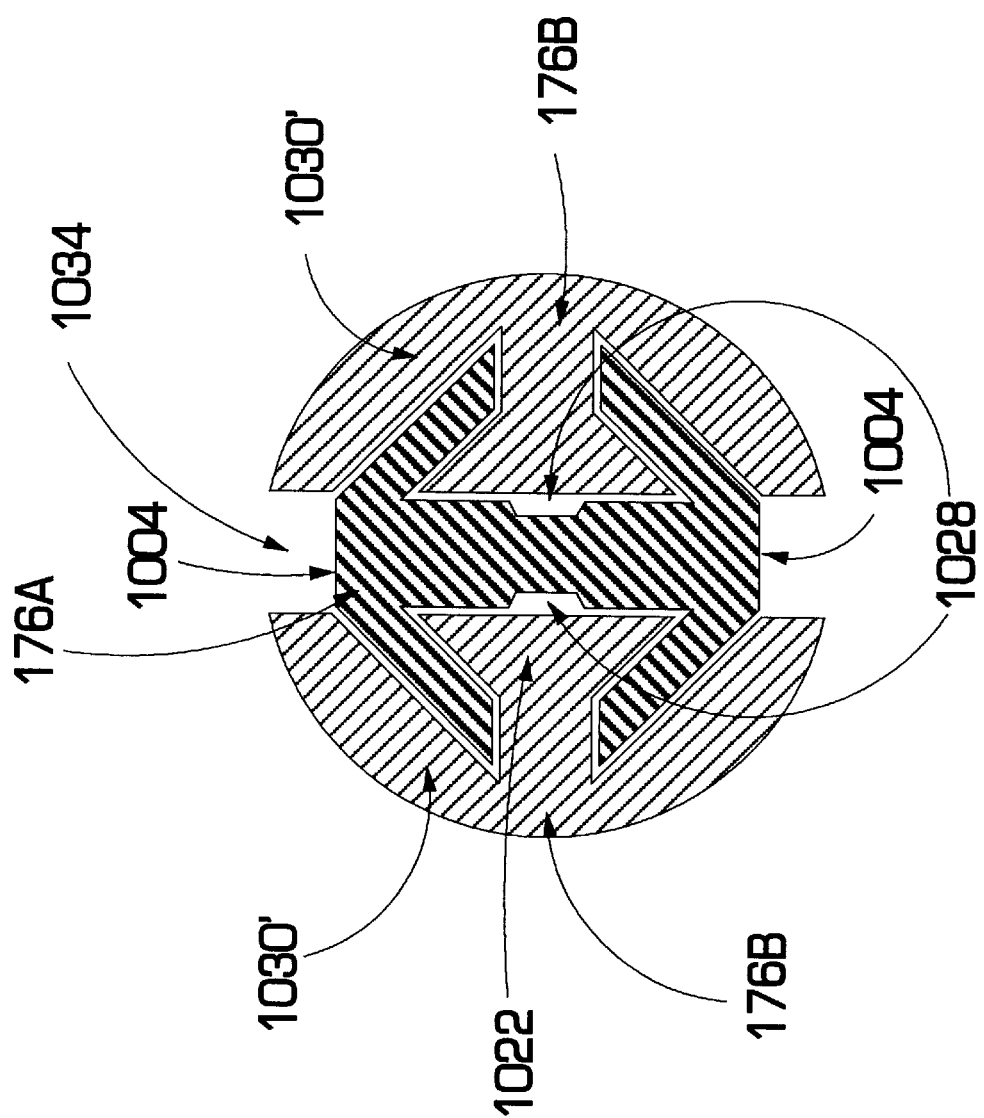

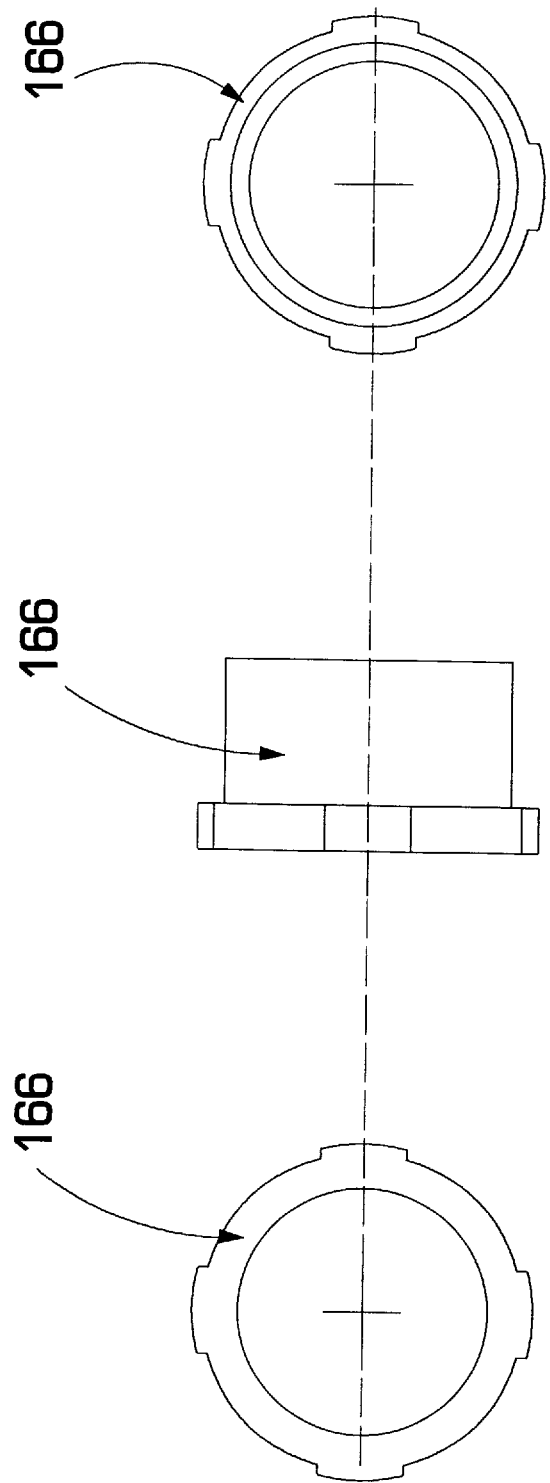

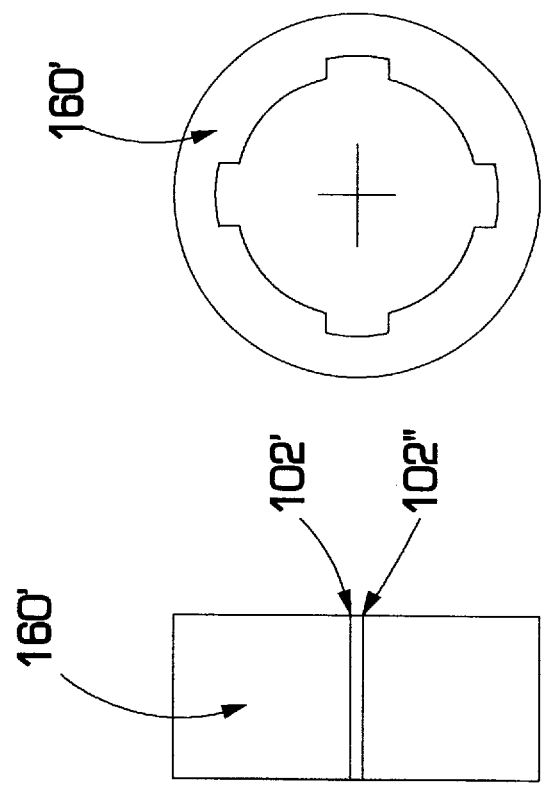

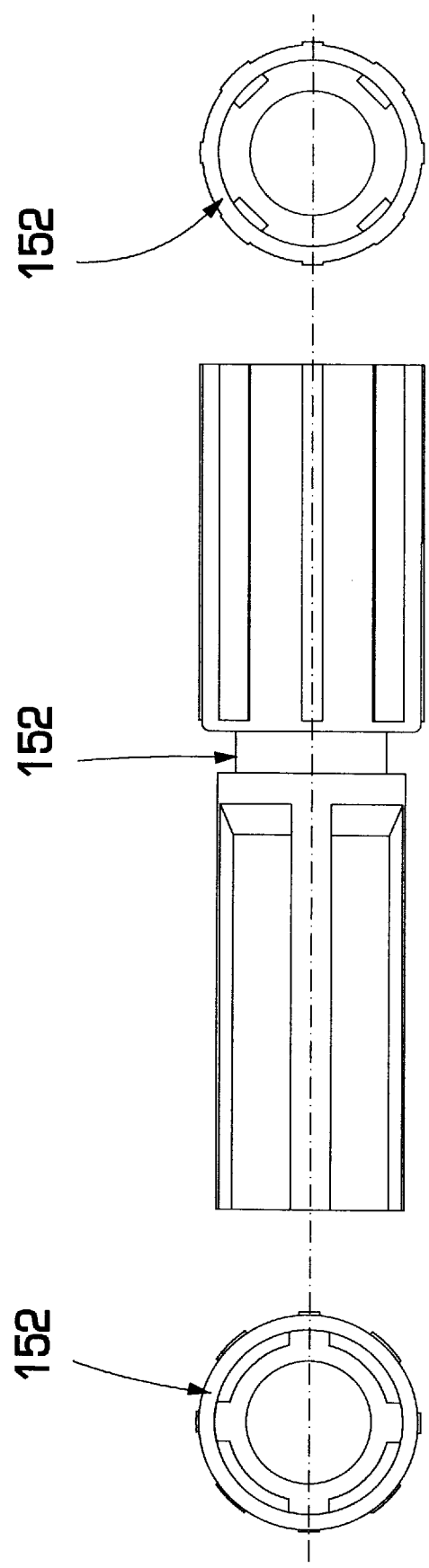

PEN-TYPE INJECTOR DRIVE MECHANISM

RELATED APPLICATIONS

This is a continuation of U.S. Provisional application Ser. No. 60/003,409 filed Sep. 8, 1995.

FIELD OF THE INVENTION

This invention relates to drive mechanisms for pen-type injectors, and more particularly to permanently engaged direct drive mechanisms for pen-type injectors that maintain a plunger on a piston of a medication cartridge in a pen-type injector.

BACKGROUND OF THE INVENTION

Several different types of pen-type injector drive mechanisms have been developed over the years. These have been used with a variety of pen-type injectors to administer an injection of fluid such as insulin.

One type of pen-type injector drive mechanism simply uses a push pump injector mechanism. To administer an injection, a user places the needle under the skin and repeatedly presses the injection button to inject a plurality of small dosages to inject a cumulative amount of required medication. This type of drive mechanism suffers from several drawbacks. For instance, the constant pumping of the device can aggravate the injection site causing injury and pain. Also, a user must keep track of the number of depressions to determine if the proper amount of cumulative doses of medication have been injected.

Another type of pen-type injector drive mechanism uses a ratcheted plunger rod that allows a user to inject the medication with a single depression of the pen-injector. The ratchet on the plunger rod prevents the plunger rod from moving backward when the pen-injector is being adjusted or when the pen-type injector is not in use. However, this pen-type injector drive mechanism also suffers from several drawbacks. Typically, this drive mechanism is a one-way device and any incorrect dosages cannot be reset, so that the user must expel the incorrect injection amount and start over—thus, wasting medication. Also, in this type of drive mechanism, the plunger rod extends out of the pen-type injector for a considerable length when a new medication cartridge is inserted in the pen-type injector, and only shortens as injections are given. Thus the device is awkward to use and transport, since the plunger rod often gets in the way when it is at its full length with a new cartridge.

Still another type of pen-type injector drive mechanism utilizes a complicated multi-piece direct drive mechanism that pulls the plunger away from a piston in the medication cartridge when the medication dosage is adjusted and set. While more accurate and convenient to use than the previously discussed mechanisms, this injector drive mechanism suffers from several drawbacks. For example, since the plunger is pulled away from the piston in the medication cartridge, the hydraulic load that maintains the pressure in the medication cartridge is removed and the fluid may leak out, or the rubber casket in the medication cartridge may change position which could result in inaccurate dosing.

In a still further type of pen-type injector drive mechanism, the plunger rod is again formed from a plurality of pieces, and plunger rod may remain in position against the medication cartridge, while the dosage for an injection is being adjusted. However, the drive mechanism suffers from several drawbacks, since this type of injector drive mechanism is an indirect drive mechanism, which requires the user to perform a number of adjustments in order to administer an injection. For example, the user must first disengage a driving portion of the drive mechanism from the plunger portion that remains against the medication cartridge. Then the user sets the dosage of the medication. Once the dosage is set, the user must re-engage the driving portion of the drive mechanism with the plunger portion, and then inject the medication. In addition, disengaging and reengaging the drive mechanism with the plunger portion may result in slight dosage inaccuracies.

SUMMARY OF THE INVENTION

It is an object of an embodiment of the present invention to provide an improved direct drive mechanism for a pen-type injector, which obviates for practical purposes, the above-mentioned limitations.

According to one embodiment of the invention, a medication injection mechanism, for delivering a dosage of medication from a medication cartridge having a piston, includes a two-piece drive shaft, a rachet mechanism, and a drive mechanism.

In preferred embodiments, the two-piece drive shaft includes a plunger portion and a drive portion. The plunger portion has an end that contacts the piston of the medication cartridge, ratchet teeth, members or ratchet receiving means disposed on the sides of the plunger portion that define a thickness of the plunger portion, and an opening to provide a passage through the plunger portion of the two-piece drive shaft. The drive portion is formed by rails that are coupled together by a connector that passes through the opening in the plunger portion so that the drive portion is coupled to the plunger portion and can move relative to the plunger portion. Each of the rails forming the drive portion has threads on a surface that extends beyond the defined thickness of the plunger portion.

In particular embodiments, the ratchet mechanism engages with the ratchet teeth, members or ratchet receiving means of the plunger portion to permit the movement of the plunger portion towards the piston of the medication cartridge and to inhibit movement of the plunger portion away from the piston of the medication cartridge. Also, the drive mechanism engages with the threads on the rails of the drive portion, but is free of contact with the ratchet teeth, members or ratchet receiving means on the plunger portion to adjust the position of the drive portion relative to the plunger portion so that the drive portion can be moved toward the piston of the medication cartridge a fixed distance and the plunger portion is moved a distance that is less than or equal to the fixed distance.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

FIG. 2 is a front perspective view of the embodiment of the pen-type injector shown in FIG. 1.

FIG. 3 is a partial cross-sectional and exploded side view of the pen-type injector shown in FIG. 2.

FIGS. 7(a)–7(i) show exploded views and details of a drive mechanism in accordance with an embodiment of the present invention. FIG. 7(a) is an exploded view of the drive mechanism. FIGS. 7(b) and 7(b) are an alternative embodiment for a portion of the drive mechanism. FIG. 7(d) is a further exploded view of an actuator knob drive shaft shown in FIG. 7(a). FIGS. 7(e)–7(f) show various views of a keyway bore in the actuator knob drive shaft shown in FIG. 7(a). FIGS. 7(g)–7(i) show various views of the threaded drive shaft shown in FIG. 7(a).

FIG. 22B is a cross-sectional view of the plunger portion and a drive portion of the split, two-piece, threaded drive shaft coupled together to form a complete split, two-piece, threaded drive shaft in accordance with the embodiment of the drive portion shown in FIG. 20B.

FIGS. 23A–C are various views of a spring tensioner collar in accordance with the embodiment shown in FIG. 14.

FIGS. 27A–C are various views of a round drum in accordance with the embodiment shown in FIG. 14.

FIGS. 29A–C are various views of a dosage knob drive shaft in accordance with the embodiment shown in FIG. 14.

DETAILED DESCRIPTION OF THE PREFERRED EMBODIMENTS

Figure 1:
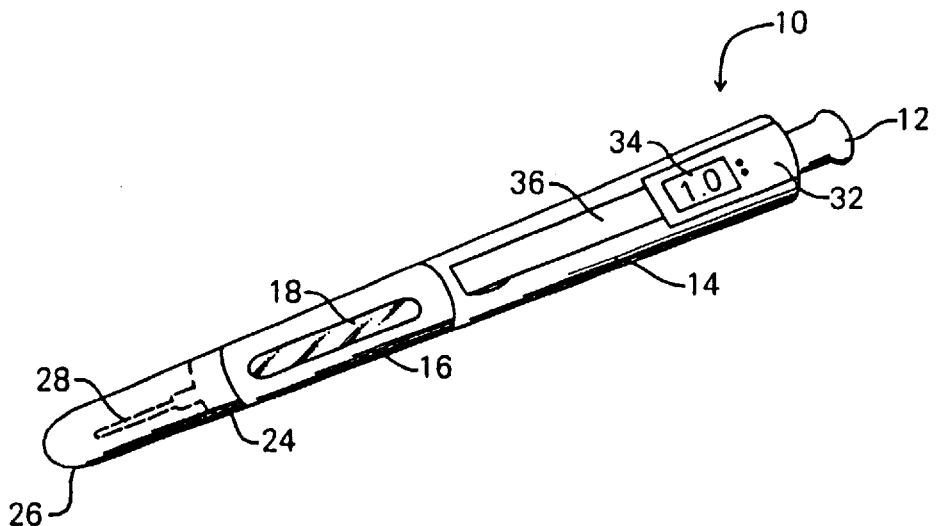
FIG. 1 is a perspective view of a pen-type injector in accordance with an embodiment of the present invention.
Figure 4:
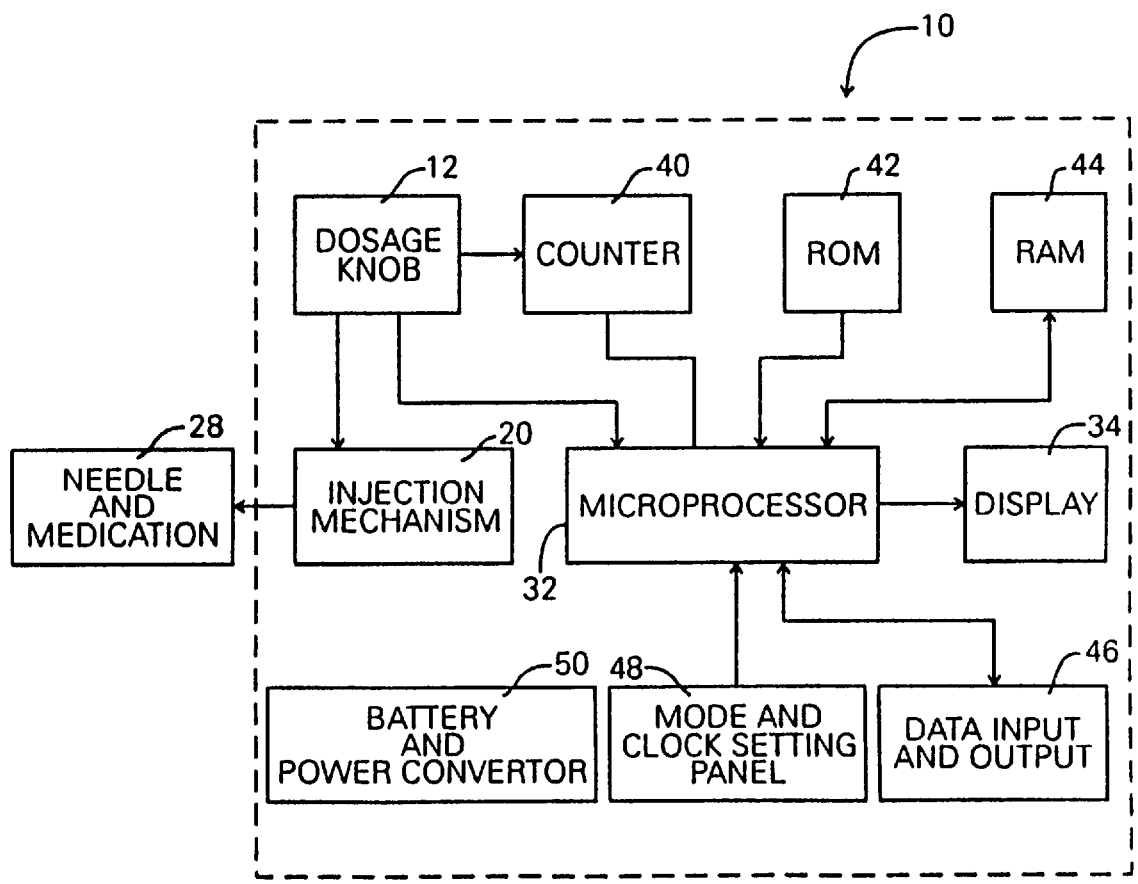
FIG. 4 is a simplified block flow diagram for the pen-type injector as shown in FIG. 1.

As shown in the drawings for purposes of illustration, the invention is embodied in an improved drive mechanism which uses a split, two-piece drive shaft to provide improved dosage delivery.

FIGS. 1–4 show one embodiment of a pen injector that utilizes a solid, one-piece drive shaft that was described in U.S. patent application Ser. No. 08/396,420 filed Feb. 28, 1995, and which is incorporated herein by reference. Operation of this embodiment of the drive mechanism shown in FIGS. 1–4 is relatively simple. The user prepares the pen-type injector 10 by depressing the start button 38 to activate the microprocessor 32. If a new medication cartridge 22 is required, the user unscrews the medication cartridge housing 16 from the injection mechanism housing 14, and couples a pre-filled medication cartridge 22 to the injection mechanism 20 and the injection mechanism housing 14. Once the medication cartridge 22 is attached, the user rescrews the medication cartridge housing 16 onto the injection mechanism housing 14. Next, the user removes the protective needle cover 26, and attaches a disposable needle 28 to the needle base 24. The user then holds the pen-type injector 10 with the disposable needle 28 pointing upward and rotates the actuator knob 12 to set a small amount of medication (typically 2–4 units). The user then depresses the actuator knob 12 to eliminate the small amount of medication and remove the air from the disposable needle 28. The user may also use a recall and delete function to delete the air removing injection from memory to prevent it from being stored with the other stored data. Alternatively, the user can mark this entry as an air removal injection, once it is stored in the memory. Depression of the actuator knob 12 delivers the set amount of medication. The system then remains on for 60 seconds (although longer or shorter times may be used) after the actuator knob 12 has been depressed so that the user can delete the most recent entry, such as an air shot. After 60 seconds (although longer or shorter times may be used), the pen-type injector powers itself down. Finally, the user reattaches the protective needle cover 26 to prevent inadvertent needle pricks or damage to the disposable needle 28.

To give an injection with the pen-type injector 10, the user removes the protective needle cover 26 and, if present, the protective needle sheath 30. The actuator knob 12 is released and the microprocessor 32 is activated. In preferred embodiments, when activated, the microprocessor 32 displays the time and the amount of the last injection on the display 34 in an alternating sequence for 5 seconds (although longer or shorter periods may be used) to remind the user of the last injection event. This substantially reduces the chance of "double dosing" (i.e., giving too much medication). After the reminder display, the pen-type injector 10 automatically zeros itself so that the user can dial in and set the dosage by rotating the actuator knob 12 in one direction (typically clockwise) until the desired amount of the medication to be injected is displayed on the display 34. In particular embodiments, the display 34 changes in real time, and in preferred embodiments, an audible click or beep is heard as the user rotates the actuator knob 12. Also in preferred embodiments, each click represents an incremental change in the dosage selected (i.e., 0.1, 0.25, 0.5 or 1.0 units). In bi-directional models, the user can increase or decrease the amount of medication to be injected. However, the microprocessor 32 will not allow the user to set a dosage below zero or to select a dosage larger than the amount of medication remaining in the medication cartridge 22. If any incorrect dosage is selected or any step in the injection process is not properly performed, an error message will be displayed on the display 34.

In further embodiments, if an injection or other function is not performed within a predetermined period of time (e.g., 1 minute or the like), the pen-type injector shuts down to conserve power in a "sleep mode." Activation of a function button or turning the dosage knob 12 will reactivate the pen-type injector 10.

After the dosage is selected, the user chooses an injection site, pushes the disposable needle 28 under the skin and depresses the actuator knob 12 down as far as it will go. The actuator knob 12 automatically locks in the depressed position when the actuator is depressed completely and the injection is completed. When the actuator knob 12 is depressed, the microprocessor 32 stores the injection event in the RAM 44 by the date, the time and the amount of injected medication. When the user returns home, or after a certain number of injections have been administered, the user can activate the microprocessor 32 with the mode and clock setting panel 48 to review the recorded data as it is displayed on the display 34. The patient can then transcribe this information in a separate log book if desired. When the user visits the doctor, the doctor can download all the stored injection information into an external computer via the data I/O port 46 to produce a report. The doctor can then review the data to spot trends and determine compliance with the medical regimen. If required, the doctor can update the program instructions in the pen-type injector 10 via the data I/O port 46 to provide reminder alarms at various times.

Figure 5:
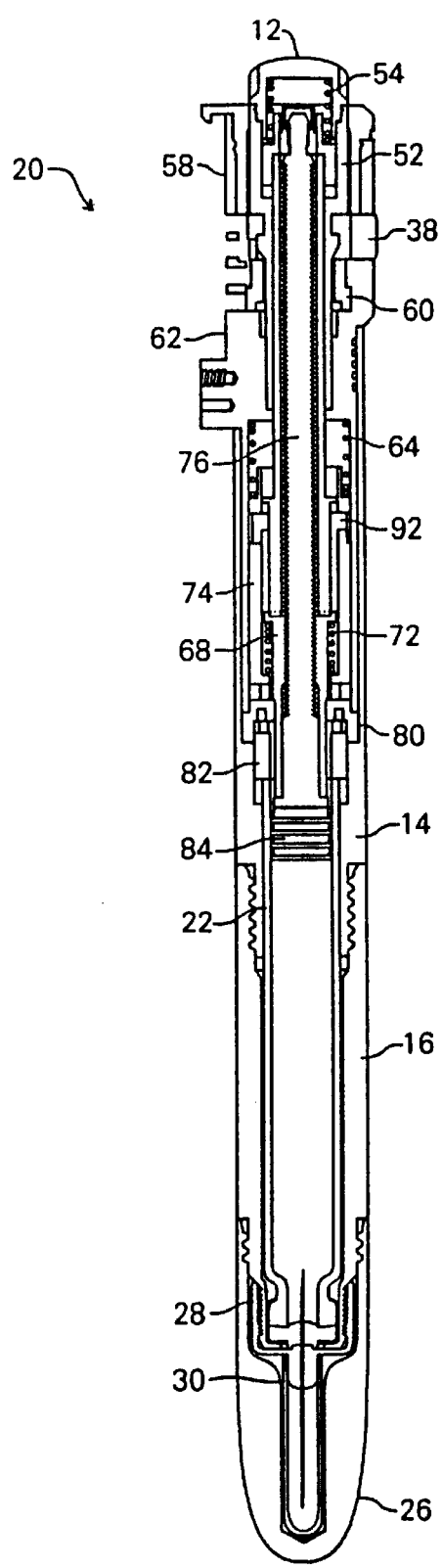
FIG. 5 is a cross-sectional view of the pen-type injector embodiment as shown along the line 5—5 in FIG. 2.
Figure 6:
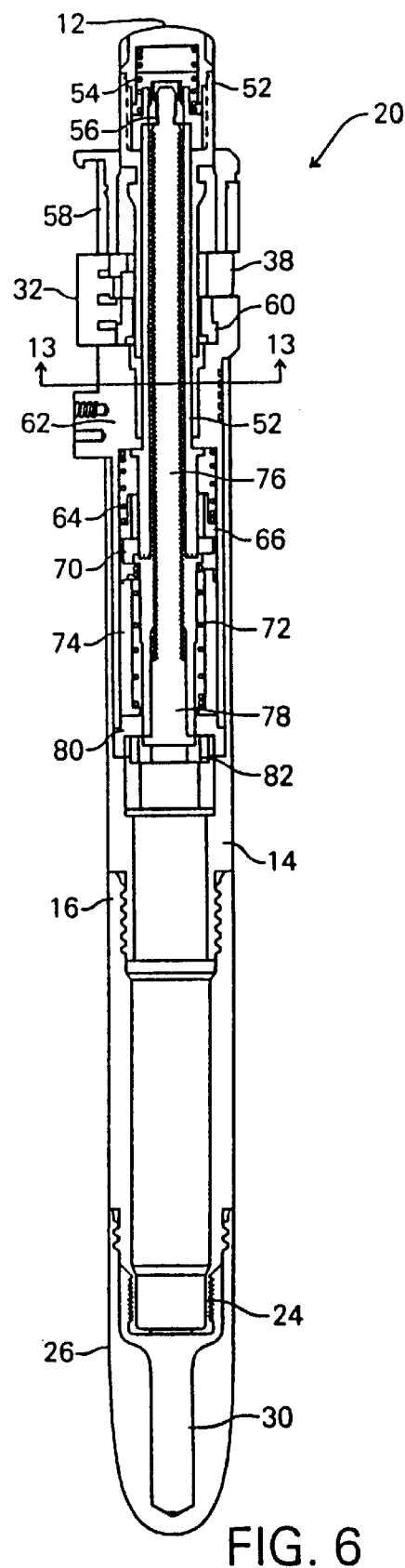
FIG. 6 is another cross-sectional view of the pen-type injector shown in FIG. 5, with the actuator in the released position.
Figure 13:
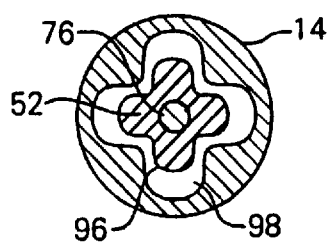
FIG. 13 is a cross-sectional view of the pen-type injector as shown along the line 13—13 in FIG. 6.

FIGS. 5 and 6 show detailed cross-sectional views of a preferred embodiment of a direct drive injection mechanism 20 as shown along the line 5—5 in FIG. 2. FIGS. 7(a)–7(i) show exploded views and details of the direct drive mechanism 20. FIGS. 8–12 show various views that detail the drive mechanism 20 shown in FIGS. 5 and 6. FIG. 13 is a cross-sectional view of the drive mechanism 20 along the line 13—13 shown in FIG. 6. The drive mechanism 20 includes a dosage knob drive shaft 52, a tension spring 54, a lock nut 56, a display seat 58, an offset camshaft 60, an electronics mount 62, a ratchet spring 64, a ratchet collar 66, a drive calibrator 68, a ratchet gear 70, a synchronizer spring 72, a stationary synchronizer 74, a threaded drive shaft 76, a plunger 78, an end cap 80, a medication cartridge tensioner and synchronizer 82, and a medication cartridge piston 84 that are coupled as shown in FIGS. 5–12.

Figure 7A:
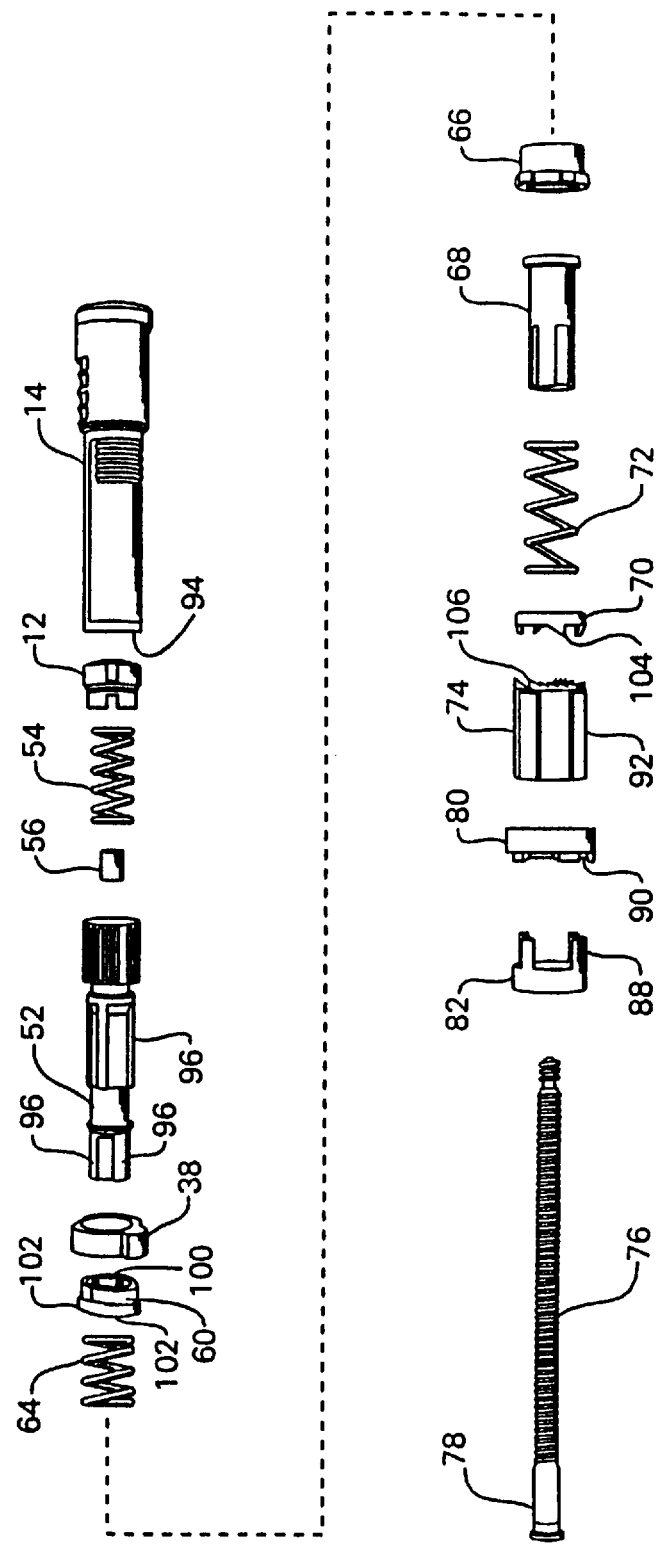
Figure 8:
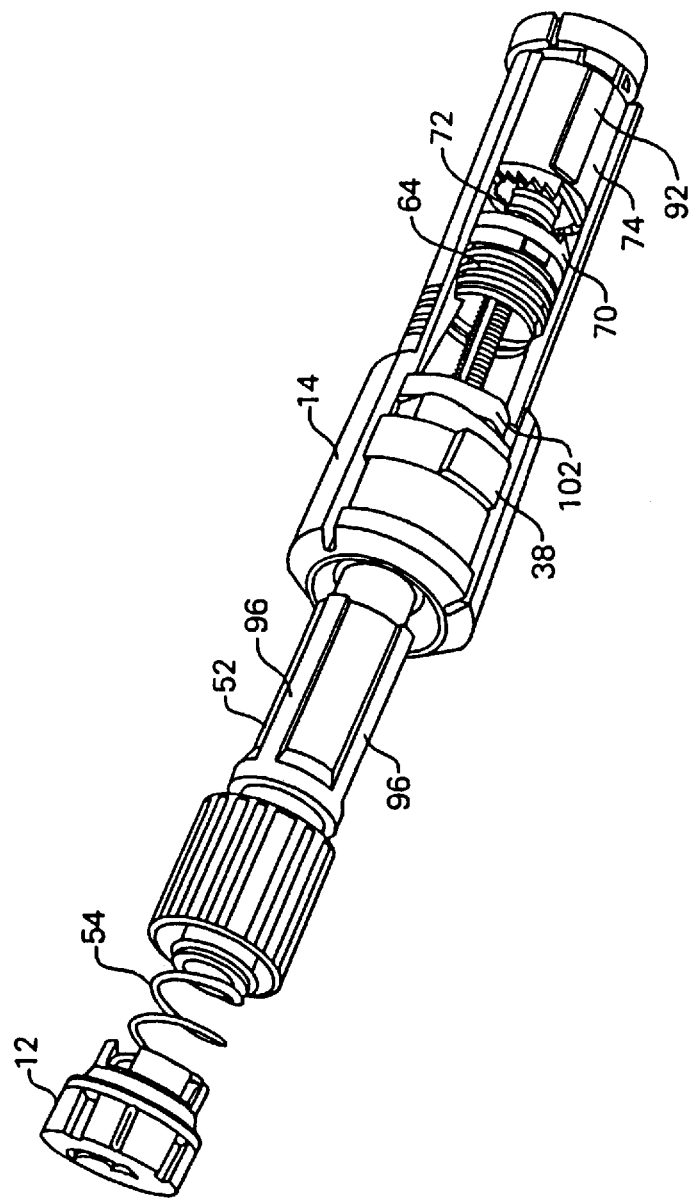
FIGS. 8–12 show various views of the drive mechanism in accordance with an embodiment of the present invention.
Figure 9:
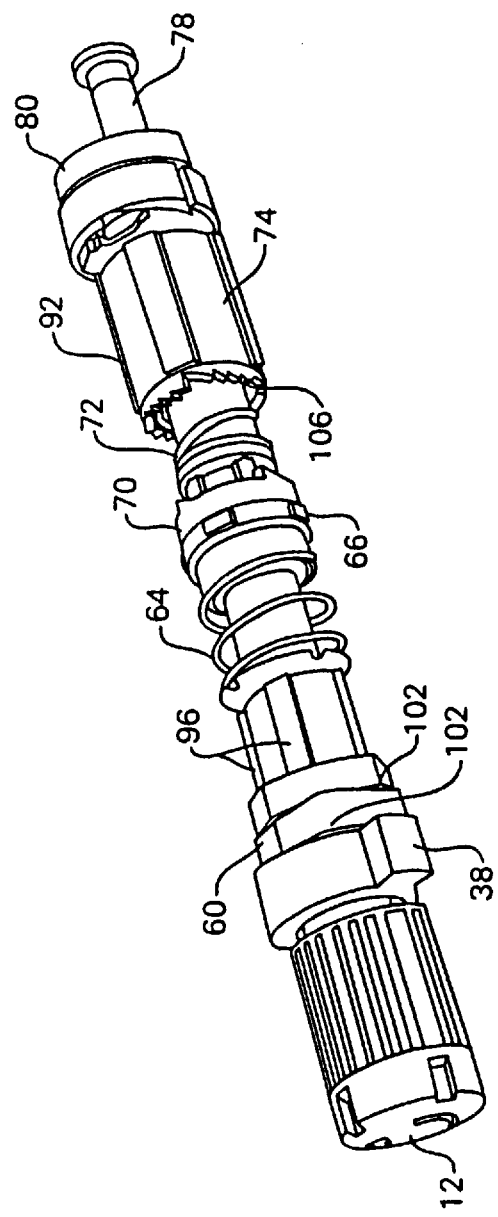
Figure 10:
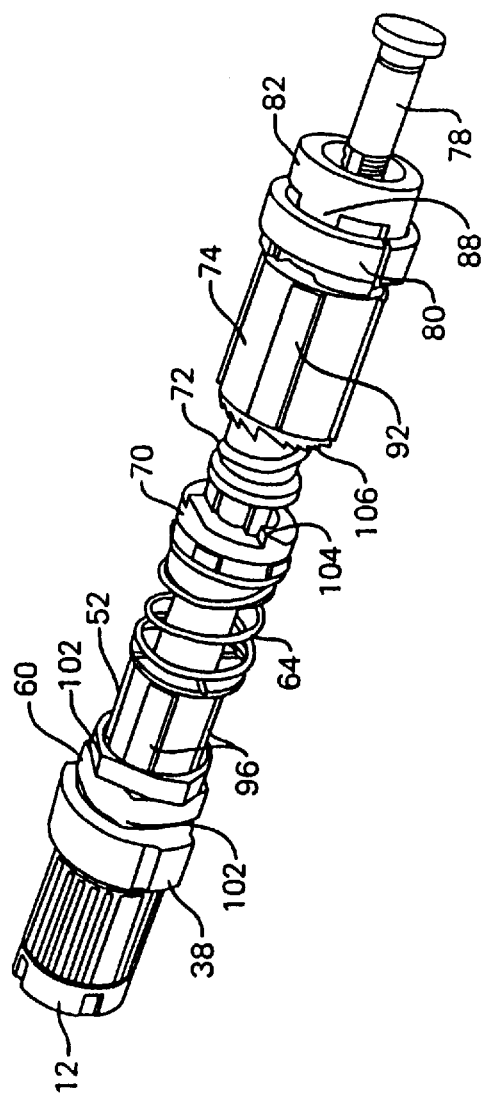
Figure 11:
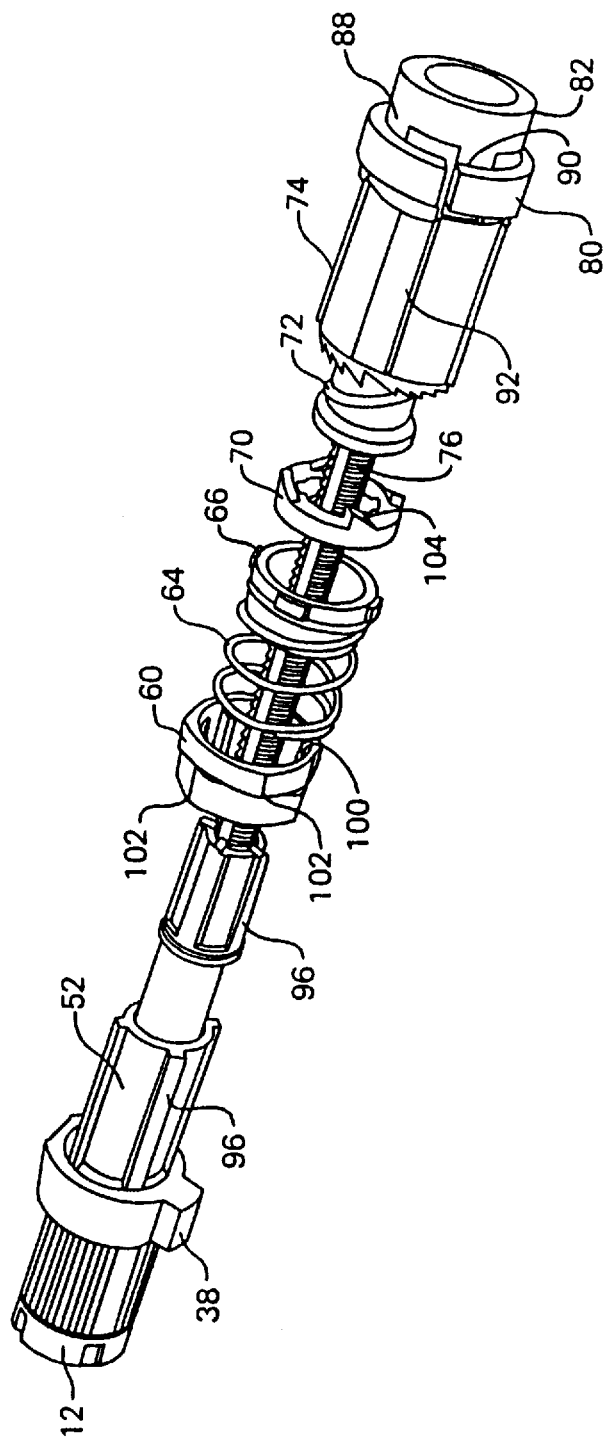
Figure 12:
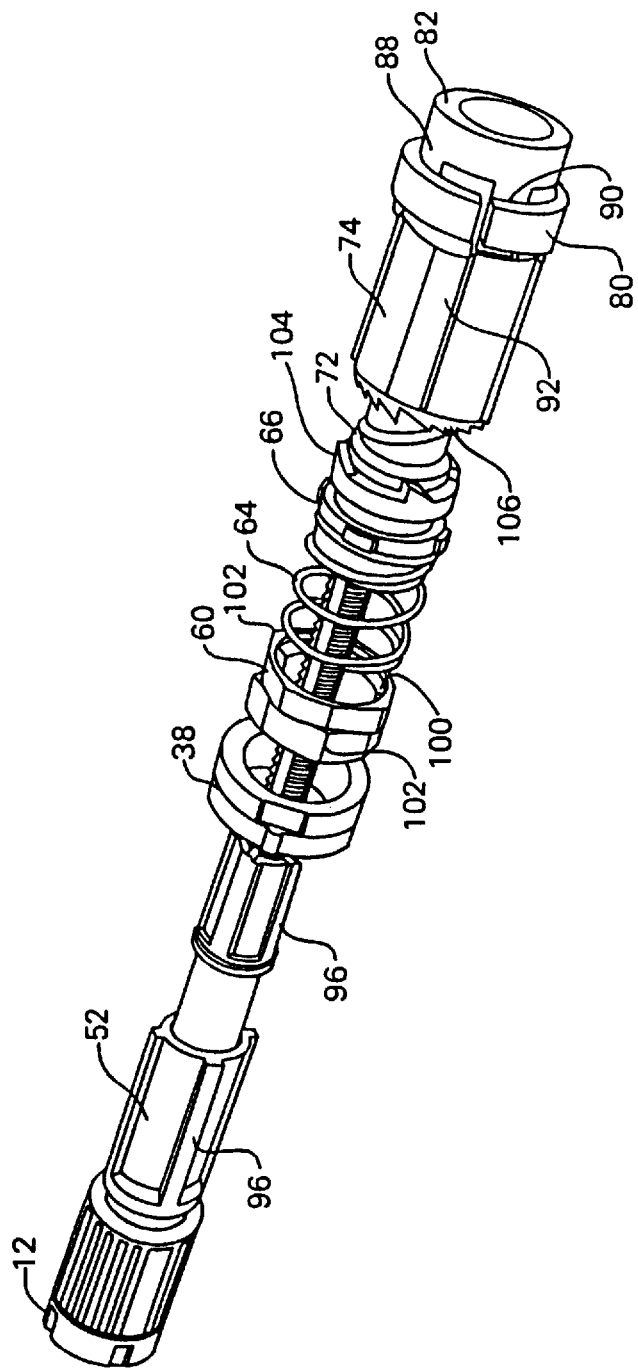

The dosage knob drive shaft 52 is coupled to a splined dosage actuator 53 by a splined retainer 55 (see FIGS. 7(a) and 7(d)). The splines 96 of the dosage knob drive shaft 52 are timed to the splines 96A of the splined dosage actuator 53 at a 45° rotational offset (alternative embodiments may use other angular rotational offsets). The offset is referenced by the pre-determined fixed location of the splined retainer 55 during assembly to the tubular end of the drive shaft 52. The dosage knob drive shaft 52, the dosage actuator 53, the splined retainer 55 and the dosage actuator knob 12 form a sub-assembly. The sub-assembly is coupled to the threaded drive shaft 76 by a left-handed threaded locknut 56. The threaded drive shaft 76 has a double keyway that runs the entire length of the threads on the threaded drive shaft 76 to allow the drive shaft 76 to move laterally in a keywayed bore 57 (see FIGS. 5, 6 and 7(e)–7(i)) of the dosage knob drive shaft 52 along the centerline axis of the sub-assembly when the dosage actuator 53 is rotated in a clockwise or counter-clockwise direction for the purpose of selecting a dosage setting. The double internal keyway in the splined end of the bore of the dosage knob drive shaft 52 is used to hold the threaded drive shaft 76 in a fixed position that prevents the threaded drive shaft 76 from rotating within the sub-assembly. The left-handed threaded locknut 56 is a retainer that prevents the threaded drive shaft 76 from traveling past a stop 59 located in the end of the dosage knob drive shaft 52 (see FIG. 7(e)). The threaded locknut 56 also determines the end of the stroke for the threaded drive shaft 76, which corresponds with a pre-determined position of the threaded drive shaft 76 to signify an empty medication cartridge.

The start button 38 is also coupled to the dosage actuator 53 to maintain the dosage actuator sub-assembly in a depressed position when the pen-type injector 10 is not being used, and to release the spring tensioned dosage actuator 53 and activate the microprocessor 32 when the pen-type injector 10 is to be used for an injection. Contained within the internal housing of the dosage actuator sub-assembly is a tension spring 54 that is securely attached to the interior of the sub-assembly by the actuator knob 12. The purpose of the spring 54 is to hold the sub-assembly at a pre-determined tension to provide drive shaft dampening from the hydraulic loads produced during the injection cycle. All free tolerances in the dosage actuator sub-assembly are taken up by the tension spring 54 to maintain the sub-assembly in a stable configuration and to help ensure injection dosage accuracy. When the starter button 38 is depressed, the synchronizer spring 72 displaces the entire dosage actuator sub-assembly along with the threaded drive shaft 76 and the drive calibrator 68 to move them into the activated position to select a dosage and inject the selected dosage of medication. Tension spring 54 and ratchet spring 64 provide shock damping for the dosage actuator sub-assembly, when it is ejected to and stopped at the activated position. The synchronizer spring 72 also facilitates maintaining the plunger 78 in a proper position with respect to the insulin cartridge piston 84 when the pen-type injector 10 is not being used, so as to minimize the effects of fluid expansion or contraction that could draw air into the insulin cartridge 22 during storage and change in atmospheric pressure.

The dosage knob drive shaft 52 that is assembled with the dosage actuator 53 has splines 96 which, when the dosage actuator 53 is in the depressed position, are locked in corresponding spline slots 98 of the injection mechanism housing 14 to prevent the dosage actuator 53, the splined retainer 55, the dosage actuator knob 12, the dosage knob drive shaft 52 and the threaded drive shaft 76 from being rotated. When the dosage actuator 53 of the dosage knob sub-assembly is released by the start button 38, the dosage actuator 53, the dosage actuator knob 12 and the dosage drive shaft 52 move in a direction away from the medication cartridge 22. The splines 96 then slide clear of the spline slots 98 so that the dosage actuator 53, the dosage actuator knob 12, the dosage knob drive shaft 52 and the threaded drive shaft 76 can be rotated as a single unit. This allows the relative positioning of the threaded drive calibrator 68 and the threaded drive shaft 76 to be adjusted, resulting in the drive calibrator 68 being advanced or retarded in position to adjust the dosage of medication that will be injected by the pen-type injector 10.

The splines 96A of the dosage actuator 53 are coupled to internal spline slots 100 of the offset cam collar 60 which is coupled to the counter 40 mounted on the electronics mount 62. The offset cam collar 60 has cam lobes 102 that are in operative contact with rocker switches (contact switches or the like) on the counter 40. When the dosage actuator 53 and dosage actuator knob 12 are rotated, the dosage knob drive shaft 52, the splined retainer 55, and the dosage actuator knob 12 sub-assembly rotate the offset camshaft 60 and the cam lobes 102 to actuate the rocker switches (not shown) to increment the counter 40 by one count per each predetermined angle of rotation of the dosage actuator 53. The rotation of the dosage knob actuator knob 12 sub-assembly also changes the axial positioning of the threaded drive calibrator 68 relative to the threaded drive shaft 76. This causes the drive calibrator 68 to advance or retard in position relative to the threaded drive shaft 76 depending on the direction of rotation of the dosage actuator 53 and dosage actuator 12 to adjust the dosage of the medication to be injected. In preferred embodiments, the pre-determined angle of rotation is 90° (although larger or smaller angles may be used). Alternatively, a round drum with bar code stripes can be used in place of the offset cam collar, which would then utilize an anode/diode photosensitive receiver to facilitate counting of incremental movements of the plunger shaft in relation to the insulin cartridge septum position.

FIG. 7(c) illustrates an alternative to the offset camshaft 60 and cam lobes 102 that are operatively coupled with the rocker switches (not shown) on the counter 40. The alternative is a round drum 60' having a plurality of thin bar code lines 102' and thick bar code lines 102'' that are read by the counter through an optical sensor and light pipe (not shown). The lines 102' and 102'' are grouped in pairs of one thin line 102' next to one thick line 102''. The pairs are spaced at predetermined angles around the round drum 60' to represent increments to increase or decrease the dosage amount to be injected. In preferred embodiments, the pairs of lines are spaced at 90° increments around the round drum 60' (although larger or smaller increments may be used). In particular embodiments, the optical sensor senses one direction of rotation of the round drum 60' by detecting a thin line 102' followed by a thick line 102'' and then increments the counter 40 by one for each set of detected lines. Conversely, if the sensor detects a thick line 102'' followed by a thin line 102', it determines that the rotation is in the opposite direction and decrements the counter 40 by one. In alternative embodiments, the lines may be a reflective material, rather than dark bar code lines. In further alternatives, the sensor may use infrared (IR) radiation or may use optical sensors that do not require light pipes.

The display seat 58 is adapted to hold the display 34 and the microprocessor 32. The microprocessor 32 is coupled to the counter 40 that is mounted on the electronics mount 62 to determine the dosage of medication to be injected based upon the value in the counter 40. The display seat 58 may also be used to hold the clip 36 to allow the pen-type injector 10 to be carried like a pen.

The ratchet spring 64 is permanently attached to the interior of the injection mechanism housing 14. The ratchet spring 64 applies pressure to the ratchet collar 66 which in turn applies pressure to the ratchet gear 70. The ratchet gear 70 has teeth 104 that mate correspondingly with teeth 106 on the stationary synchronizer 74. The synchronizer spring 72 applies a counter-pressure on the stationary synchronizer 74 to maintain the ratchet gear 70 and the stationary synchronizer 74 in contact with each other. Thus, when the actuator knob 12 is rotated, a ratchet noise is produced as the ratchet gear 70 is rotated relative to the stationary synchronizer 74. Removal of the medication cartridge 22 reduces the pressure on synchronizer spring 72 so that the corresponding teeth 104 and 106 of the ratchet gear 70 and the stationary synchronizer 74 are disengaged. When the teeth 104 and 106 are disengaged, the actuator knob 12 can be rotated easily with minimal resistance, and the threaded drive shaft 76 can be withdrawn without resistance from the ratchet gear 70.

The stationary synchronizer 74 also has splines 92 which are coupled to corresponding spline slots 94 in the injection mechanism housing 14 to prevent the stationary synchronizer 74 from rotating. However, the splines 92 are slidably coupled to the spline slots 94 so that the stationary synchronizer can slide back and forth within the injection mechanism housing 14. This allows the medication cartridge 22 to increase the tension of the synchronizer spring 72 when the medication cartridge 22 is seated, and this increased tension causes the teeth 104 and 106 to engage.

FIGS. 7(a), 7(d)–(i) and 8–12 illustrate a drive mechanism utilizing a mono-directional ratchet gear 70 and a corresponding mono-directional stationary synchronizer 74. The teeth 104 and 106 on the ratchet gear 70 and the synchronizer 74, respectively, are shaped to permit setting the dosage in only a single direction. Thus, if a user goes past the required dosage, the user must either completely reset the pen or eject the currently set dosage. FIG. 7(b) illustrates an alternative bi-directional ratchet gear 70' and a corresponding bi-directional stationary synchronizer 74' having teeth 104' and 106', respectively. The shape of the teeth 104' and 106' are symmetrical, as opposed to the right angular teeth 104 and 106 on the gear 70 and synchronizer 74, to permit the dosage set by the counter 40 and displayed on the display 34 to be increased and decreased. Thus, users can correct the set dosage if they go past the desired dosage amount, without having to reset the pen or ejecting the incorrectly set dosage.

The drive calibrator 68 is threaded onto the threaded drive shaft 76 to determine the minimum and maximum positions in which the threaded drive shaft 76 can be moved to inject medication from the medication cartridge 22. The drive calibrator 68 also performs as a rotational reference point to keep track of the incremental movement of the threaded drive shaft 76 so that the dosage of medication injected by the pen-type injector can be accurately determined. An end of the drive calibrator 68 has splines 88 that engage corresponding spline slots 90 in the end cap 80 to hold the drive calibrator 68 in a rotationally fixed position. The other side of the end cap 80 is coupled to the medication cartridge tensioner and synchronizer 82 which is used to secure a medication cartridge 22 to the injection housing 14. The threaded drive shaft 76 is coupled to the medication cartridge piston 84 to inject medication in the medication cartridge 22 when the actuator knob 12 is depressed.

The illustrated direct drive mechanism only requires a single complete depression of the actuator knob 12 to inject different set amounts of medication. The illustrated direct drive allows the user to accurately set various dosage values to be injected. The drive mechanism 20 is capable of providing dosage accuracies of between 0.1 to 1.0-unit increments. However, one drawback to this embodiment is that the plunger 78 is withdrawn from the piston 84 of the medication cartridge 22 when the dosage is to be set. This removes the constant pressure on the medication cartridge 22, and the piston 84 could back out of the medication cartridge, if the injector is subjected to a shock while setting the dosage or is dropped while the actuator knob 12 is released.

FIGS. 14–29C illustrate another embodiment of a drive mechanism that utilizes a split, two-piece, threaded drive shaft to provide accurate medication dosing, and which overcomes the drawbacks of removing the plunger from the piston in the medication cartridge. In this embodiment, the drive mechanism maintains the plunger portion of the split, two-piece, threaded drive shaft in contact with the piston of the medication cartridge at all times, except for when a cartridge is being inserted or removed. This configuration prevents the piston from backing out and keeps the medication under constant pressure. The actuator knob of the drive mechanism adjusts a drive portion of the split, two-piece, threaded drive shaft surrounding the plunger portion of the split, two-piece, threaded drive shaft to set the dosage. When the actuator knob is depressed, both portions of the split, two-piece, threaded drive shaft move the end of the plunger portion forward a specified amount, and the injection is completed. The plunger portion of the split, two-piece, threaded drive shaft is not retracted away from the piston in the medication cartridge after each injection.

FIGS. 14–29C show detailed drawings of this embodiment of the present invention. Many of the parts are similar to those described above (having like numbers, with the addition of 100) and represent parts that operate similarly to the parts described above. Therefore, a detailed description of these similar parts is omitted. As shown in FIGS. 14–29C, the drive mechanism 120 includes a dosage knob drive shaft 152 (see FIGS. 29A–C), a tension spring 154, a lock nut 156, a display seat 158, a round drum 160' (see FIGS. 27A–C), an electronics mount 162, a ratchet spring 164, a spring tensioner and ratchet collar 166 (see FIGS. 23A–C), a drive calibrator 168, a ratchet gear 170' (see FIGS. 26A–C), a synchronizer spring 172, a stationary synchronizer 174' (see FIGS. 28A–C), a split, two-piece, threaded drive shaft 176 including a plunger portion 176A and drive portion 176B, a plunger 178, an end cap 180 (see FIGS. 25A–C), a medication cartridge tensioner and synchronizer 182 (see FIGS. 24A–C), and a medication cartridge piston 184.

The drive mechanism 120 is embodied in a split, two-piece, threaded drive shaft 176 that includes a plunger portion 176A and drive portion 176B. The plunger portion 176A includes a plunger 178 that rests against the piston 184 of the medication cartridge 122 to maintain the piston 184 in the forward position and to maintain the medication in the medication cartridge 122 under a constant pressure. The drive portion 176B is permanently engaged with the drive mechanism 120 to facilitate easy dosage setting and injection delivery with a minimum of actions required from the user. Like the embodiment, described above, the user releases the start button 138, sets the dosage by rotating the actuator knob 112, and injects the medication with a single depression of the actuator knob 112.

Figure 17:
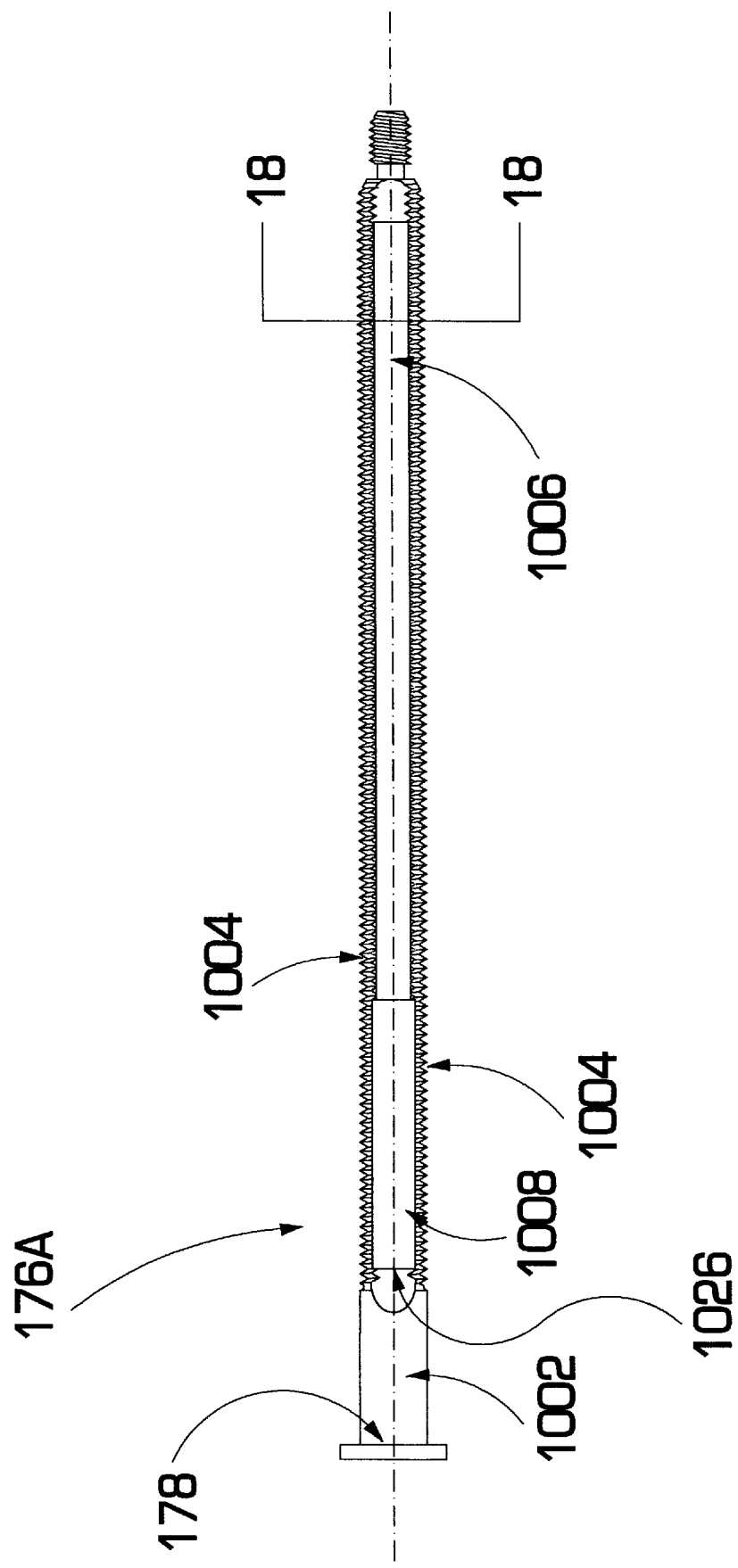
FIG. 17 is a side view of a plunger portion of the split, two-piece, threaded drive shaft in accordance with the embodiment shown in FIG. 14.
Figure 18:
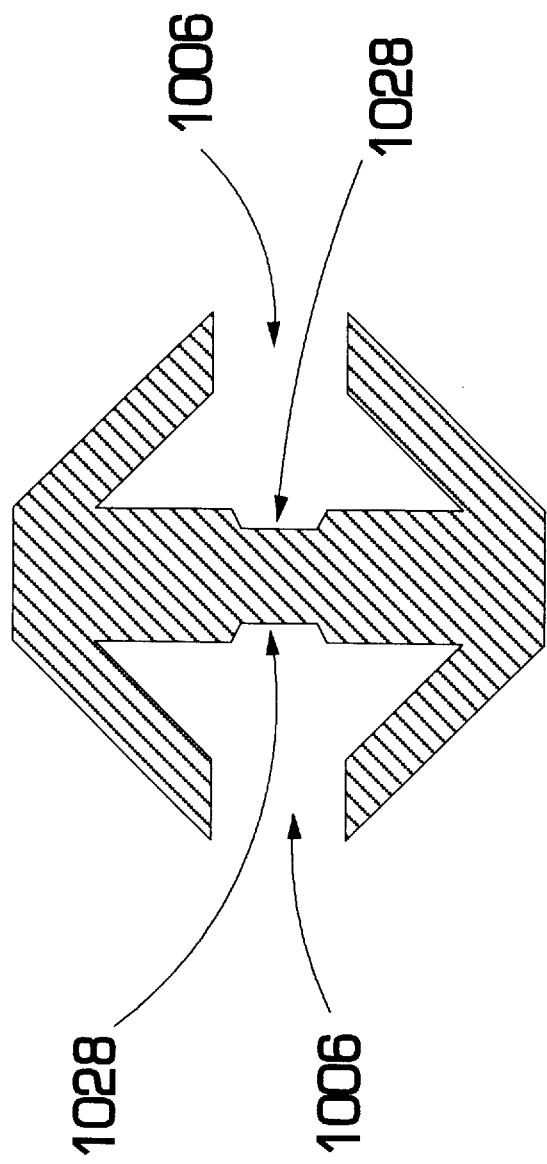
FIG. 18 is a cross-sectional view of the plunger portion of the split, two-piece, threaded drive shaft as shown along the line 18—18 in FIG. 17.

As shown in FIGS. 17 and 18, preferred embodiments of the plunger portion 176A are formed as a solid rod 1002 that has ratchet teeth 1004 on opposite sides of the rod 1002. Oriented 90° to the sides with the ratchet teeth 1004 are a pair of track slots 1006 cut into opposite sides of the rod 1002 for receiving the drive portion 176B of the split, two-piece, threaded drive shaft 176. In alternative embodiments, the ratchet teeth 1004 and the track slots 1006 may be arranged differently around the rod 1002. As shown in FIG. 18, the track slots 1006 have a substantially dovetail cross-section to facilitate rigidity and to maintain the drive portion 176B in the track slots 1006 when setting the dosage and administering an injection. In alternative embodiments, the track slots may use other cross-sectional shapes, such as rectangular, square, circular or the like. The solid rod 1002 also has openings such as an oval aperture 1008 that is cut through the rod 1002 to provide a passage from one track slot 1006 to the other track slot 1006 on the opposite side of the rod 1002. This aperture 1008 is used to limit the rearward travel of the drive portion 176B when setting a dosage to be injected. In alternative embodiments, different shape apertures, such as rectangular or the like may be used.

Figure 14:
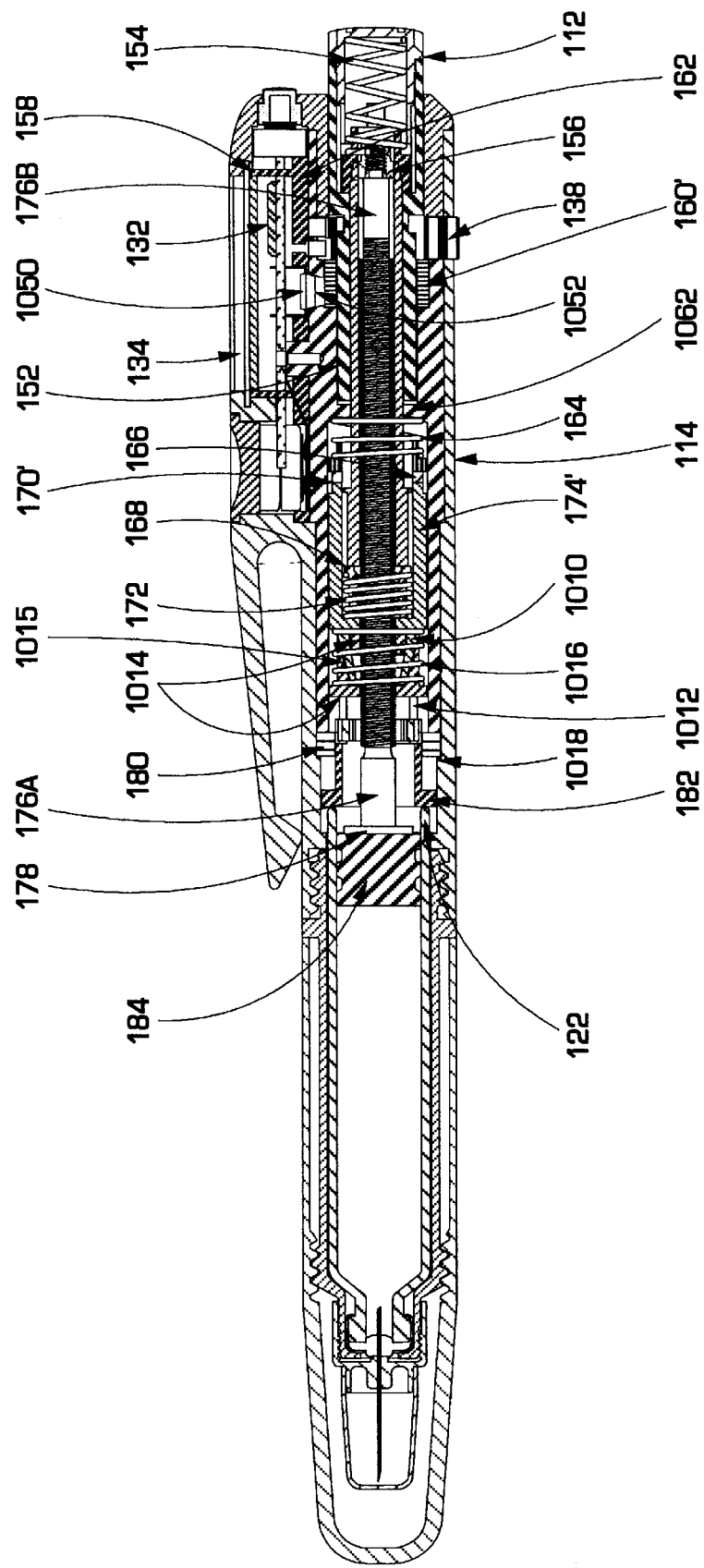
FIG. 14 is a cross-sectional view of an injection drive mechanism in accordance with an embodiment of the present invention.
Figure 15:
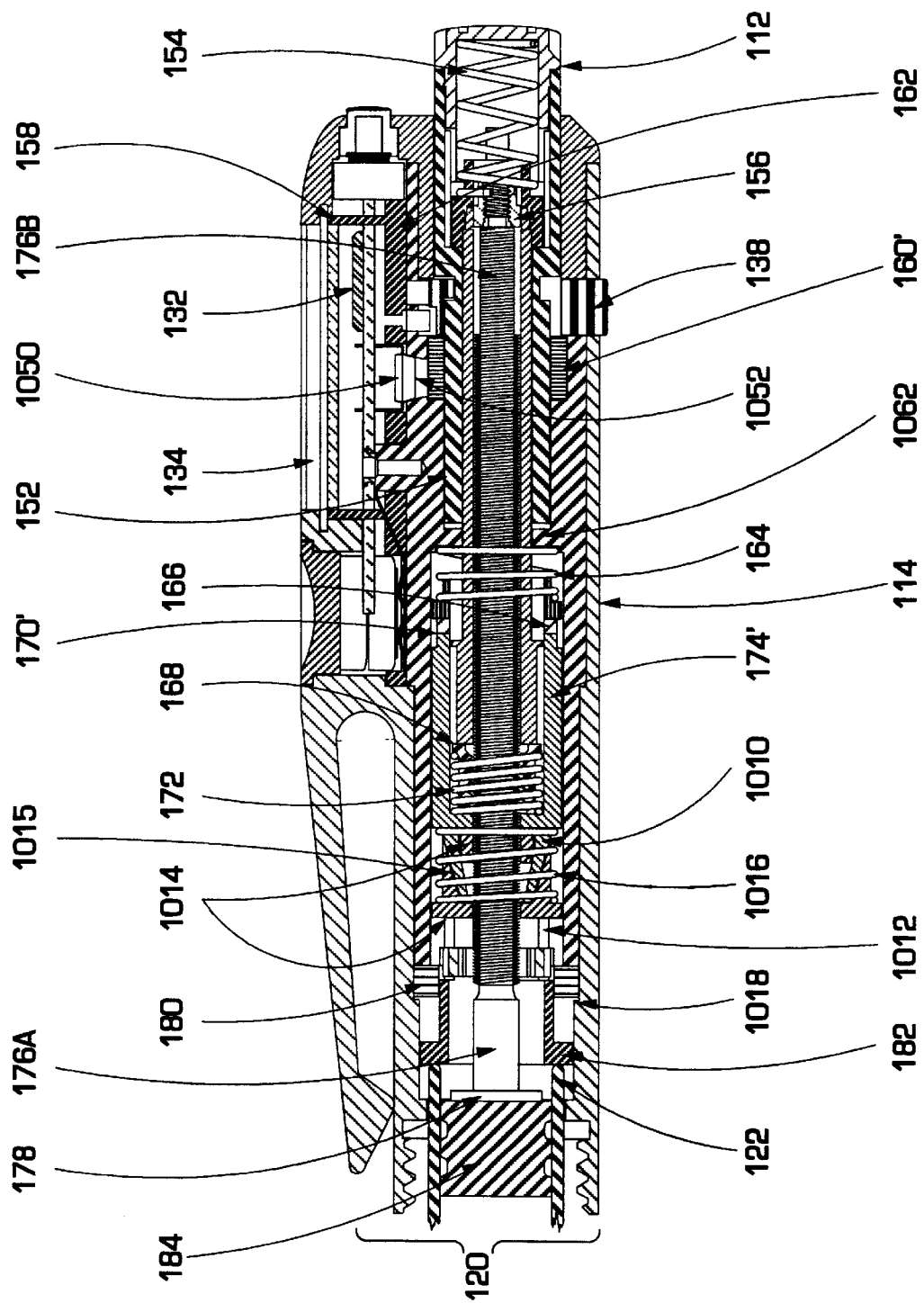
FIG. 15 is an enlarged cross-sectional view of the embodiment shown in FIG. 14.
Figure 16:
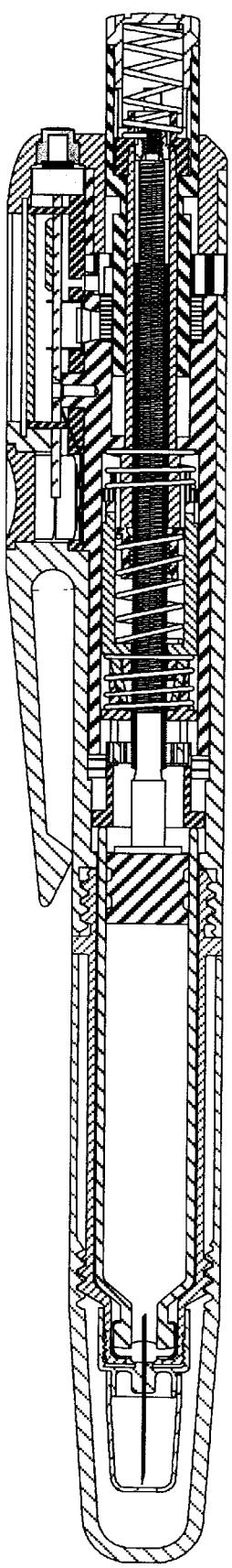
FIG. 16 is another cross-sectional view of the drive mechanism of FIG. 14 in a different axial position.

As shown in FIGS. 14–16, the ratchet teeth 1004 on the plunger portion 176A are engaged by a ratchet mechanism 1010 either formed as a part of or that is connected to the end of the stationary synchronizer 174'. The ratchet teeth 1004 are cut so that each presents a slope surface towards the medication cartridge 122 and a vertical surface towards the actuator knob 112. Thus, when the ratchet teeth 1004 are engaged with the ratchet mechanism 1010, the plunger portion 176A can move forward, but not back, when a medication cartridge 122 is coupled to the drive mechanism 120. The ratchet teeth 1004 are released when the medication cartridge 122 is removed. In alternative embodiments, different teeth shapes may be used, as long as forward movement is permitted and rearward movement of the plunger portion 176A is inhibited. In further alternative embodiments, the ratchet teeth may be replaced with grooves or the like.

The ratchet mechanism 1010 is forced to engage the ratchet teeth 1004 as the medication cartridge 122 contacts and presses against a medication cartridge tensioner and synchronizer 182, when the medication cartridge 122 is threaded onto the injection housing 114. The medication cartridge tensioner and synchronizer 182 has integral legs 1012 which pass through portals 1013 in the end cap 180 (see FIGS. 24A–25C), which is fixed to the housing 114. The integral legs 1012 contact the flat surface of a wedge cap 1014 which provides tension against the medication cartridge 122. The wedge cap 1014 is pressed back against the ratchet mechanism 1010, and the compressive force of the wedge members 1015 sliding against the ratchet mechanism 1010 forces the ratchet mechanism 1010 down into contact with the ratchet teeth 1004 of the plunger potion 176A of the split, two-piece, threaded drive shaft 176. This locks the plunger portion 176A so that it can only be pushed forward. However, when the medication cartridge 122 is removed, a ratchet release spring 1016 moves the wedge cap 1014, and the medication cartridge tensioner and synchronizer 182 with the integral legs 1012 forward towards the medication cartridge, until the medication cartridge tensioner and synchronizer 182 contacts an internal seat stop 1018 at the forward end of the injection housing 114. This releases the ratchet mechanism 1010 from engagement with the ratchet teeth 1004, so that the plunger portion 176A of the split, two-piece, threaded drive shaft 176 may be moved backward to receive a medication cartridge 122. In alternative embodiments, different ratchet mechanisms may be used so that the plunger portion 176A is inhibited from backward movement, such as a slip clutch, ratcheted camlock or the like, when a medication cartridge 122 is coupled to the injection housing 114.

Figure 19:
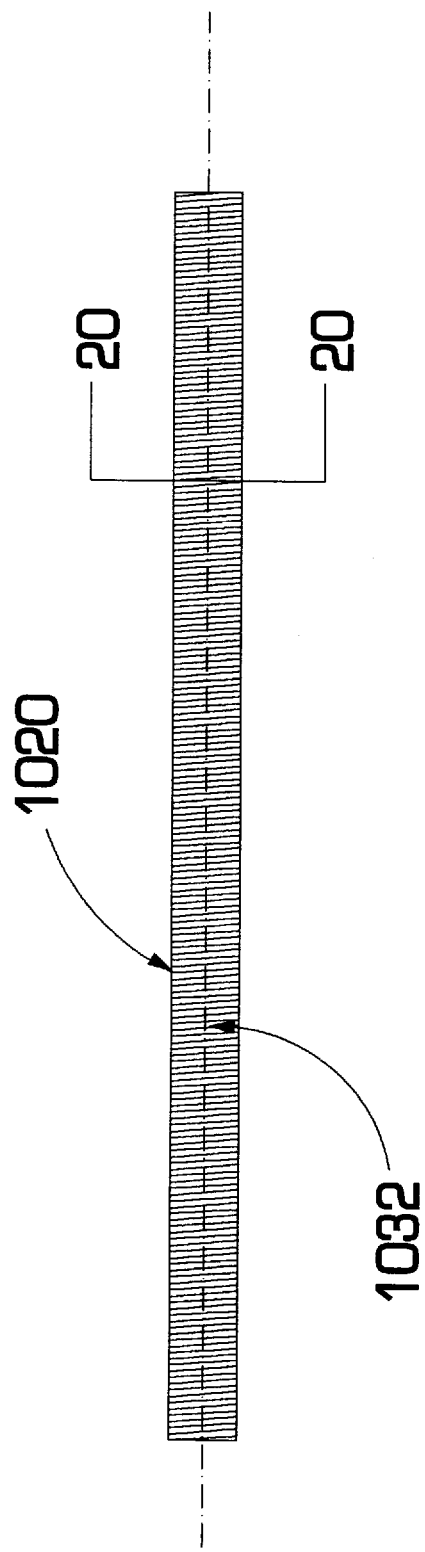
FIG. 19 is a side view of one of the pair of members that forms the drive portion of the split, two-piece, threaded drive shaft in accordance with the embodiment shown in FIG. 14.
Figure 20A:
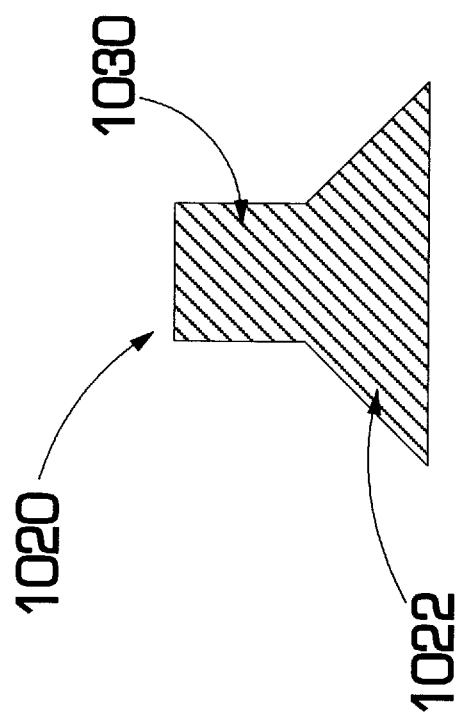
FIG. 20A is a cross-sectional view of one of the pair of members that forms the drive portion of the split, two-piece, threaded drive shaft as shown along the line 20—20 in FIG. 19.
Figure 20B:
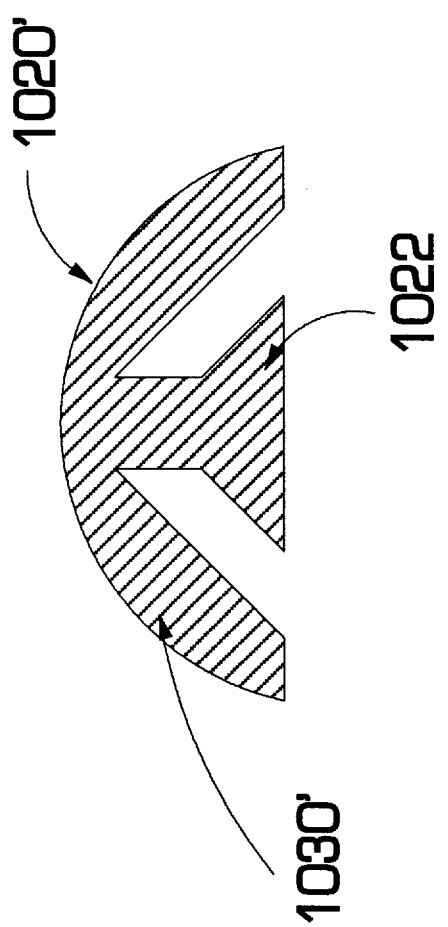
FIG. 20B is a cross-sectional view of one of a pair of members that forms a drive portion of the split, two-piece, threaded drive shaft in accordance with another embodiment.
Figure 21:
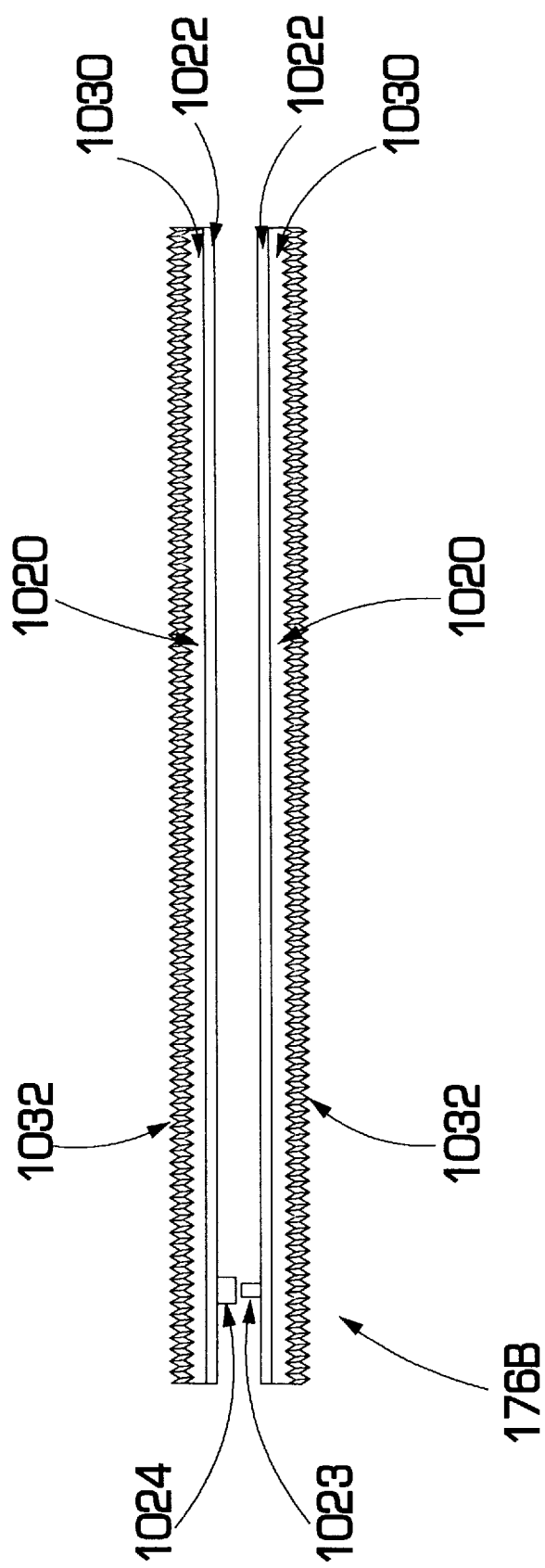
FIG. 21 is a side view of the pair of members coupled together to form the drive portion of the split, two-piece, threaded drive shaft, and which are shown oriented 90° to the plunger portion of the split drive shaft shown in FIG. 17.

As shown in FIGS. 19–21, the drive portion 176B of the split, two-piece, threaded drive shaft 176 is formed by a pair of rails 1020 that have a track portion 1022. Each of the track portions 1022 are shaped to fit within the track slots 1006 of the plunger portion 176A. The two rails 1020 are joined together by corresponding male 1023 and female 1024 connectors that pass through the aperture 1008 of the plunger portion 176A, and which are permanently joined together, by adhesives, welds, snap fit or the like. In alternative embodiments, other connection methods may be used to join the two rails 1020 together. As shown in FIG. 20A, the rails 1020 have a cross-section that matches the dovetail cross-section of the track slots in the plunger portion 176A. Once connected together, the male 1023 connector and the female 1024 connector are used to bear against an end 1026 of the aperture 1008 in the plunger portion 176A. This causes the plunger portion 176A to be pushed forward by the amount required to deliver the dosage set by the drive mechanism 120. To facilitate assembly of the drive portion 176B, each of the track slots 1006 of the plunger portion 176A includes a connector groove 1028, which is deep enough to permit the connectors 1023 and 1024 to slide in the track slots 1006 prior to being coupled together through the aperture 1008. Once coupled together, the rails 1020 contact the bottom of the track slots 1006 and cannot be removed, since the coupled connectors 1023 and 1024 prevent the rails 1020 from being withdrawn beyond a specific distance that is more than the maximum dosage that can be set by the drive mechanism 120. To further facilitate insertion of the rails 1020, the track portion 1022 of each rail 1020 in the area of the connectors 1023 and 1024 may be made slightly smaller than the cross-section of the track slots 1006. This will allow the rails 1020 to be flexed upward in the track slot 1006 to accommodate the connectors 1023 and 1024, until the connectors 1023 and 1024 reach and pass through the aperture 1008 in the rod 1002. In alternative embodiments, the connector groove 1028 may be omitted, if for example, the two rails each have a threaded bore and are connected together by a set screw or screw threaded into the threaded bore of each of the rails 1020.

Figure 22A:
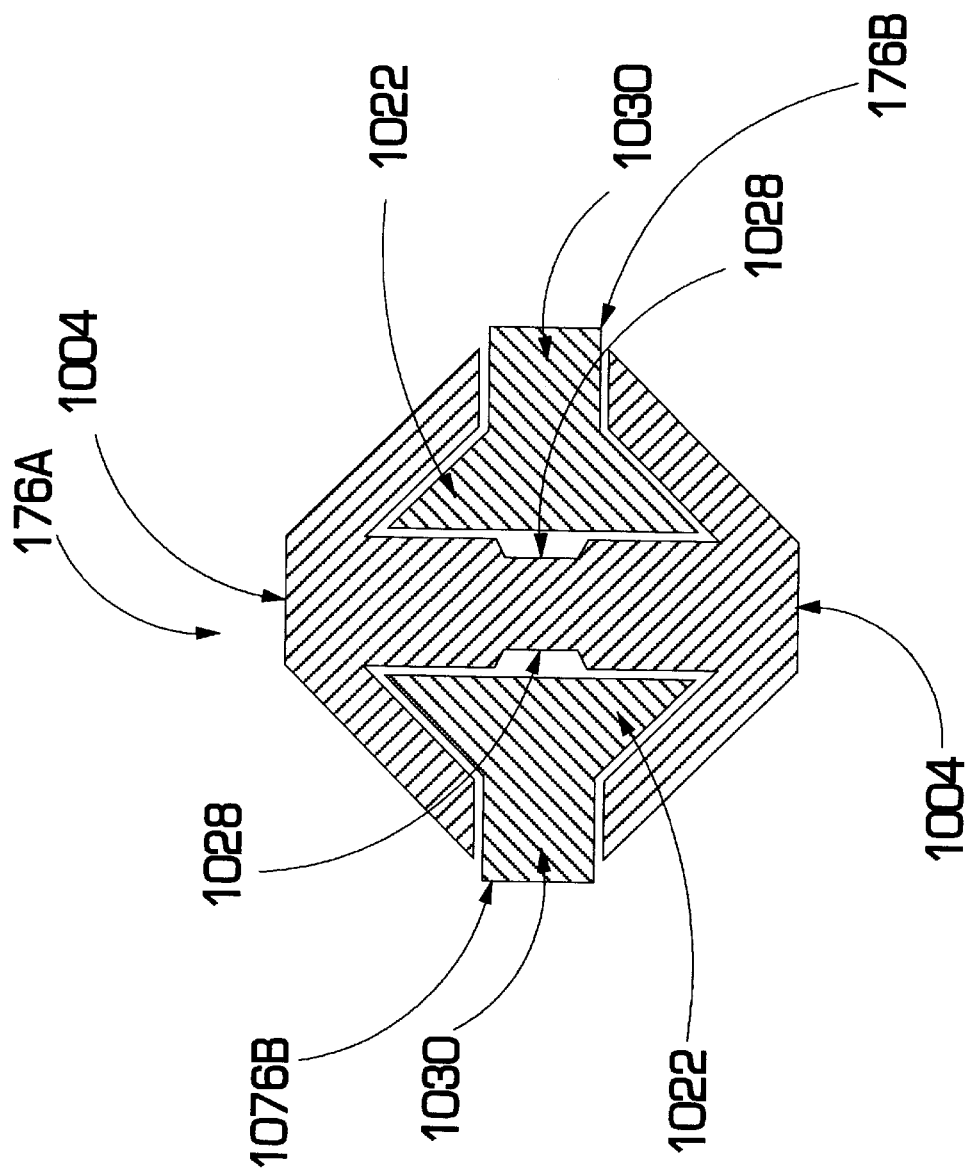
FIG. 22A is a cross-sectional view of the plunger portion and the drive portion of the split, two-piece, threaded drive shaft coupled together to form a complete split, two-piece, threaded drive shaft as shown in FIGS. 14–16.
Figures 24A, 24B, 24C:
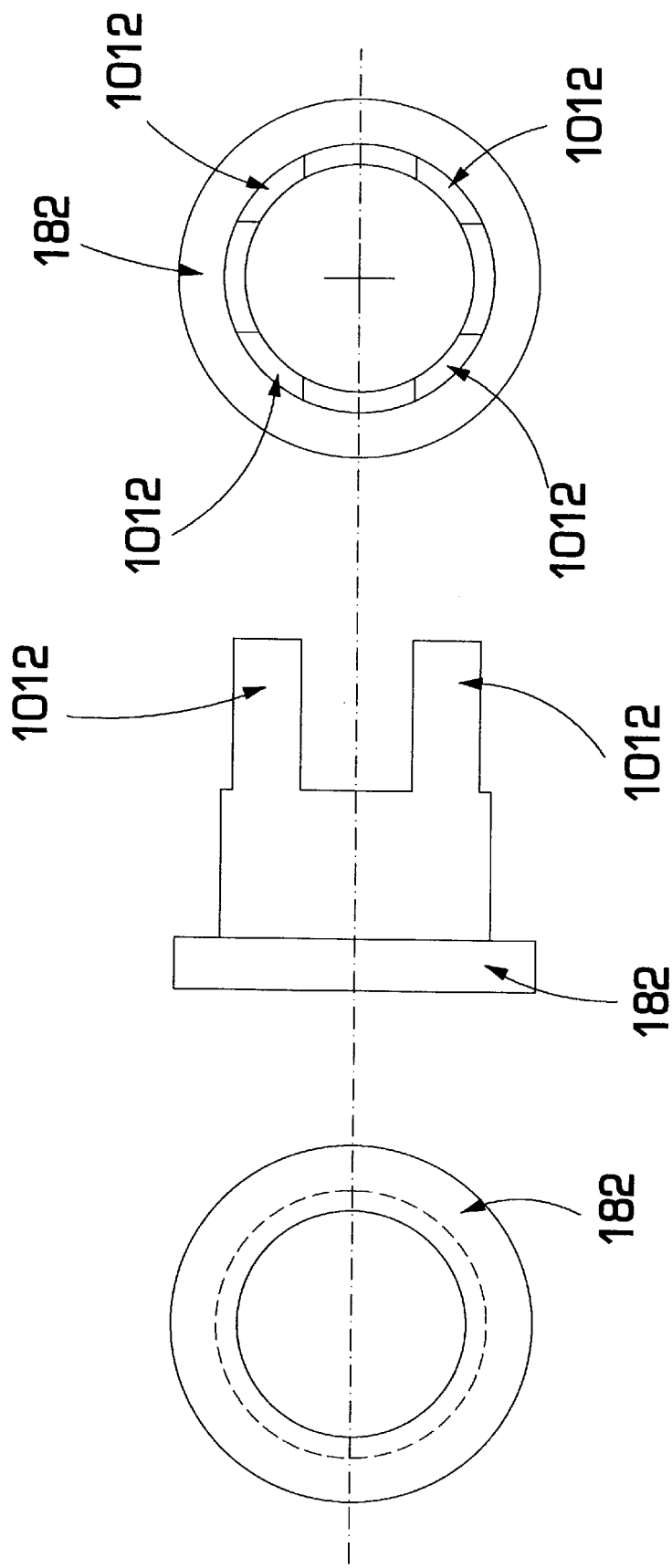
FIGS. 24A–C are various views of a medication cartridge tensioner and synchronizer in accordance with the embodiment shown in FIG. 14.
Figure 25C:
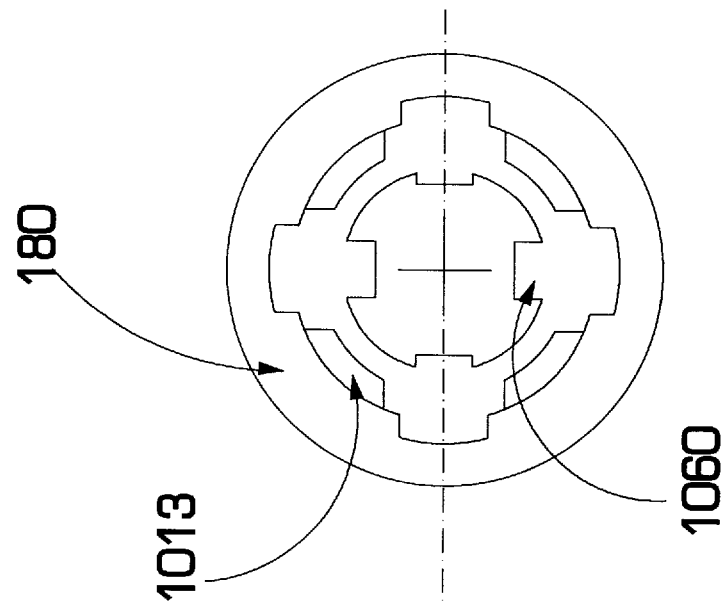
FIGS. 25A–C are various views of an end cap in accordance with the embodiment shown in FIG. 14.
Figure 25B:
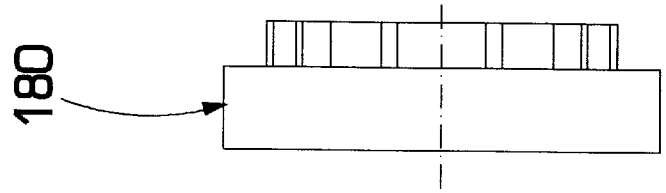
Figure 25A:
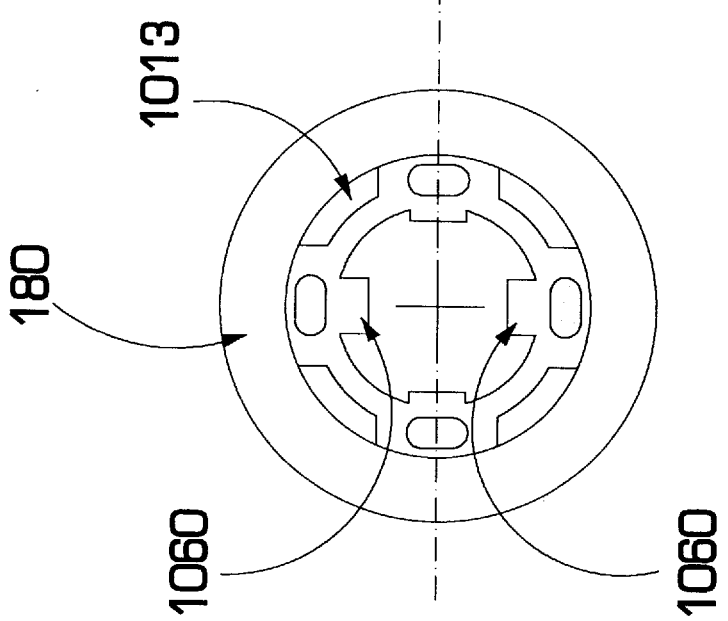
Figures 26A, 26B, 26C:
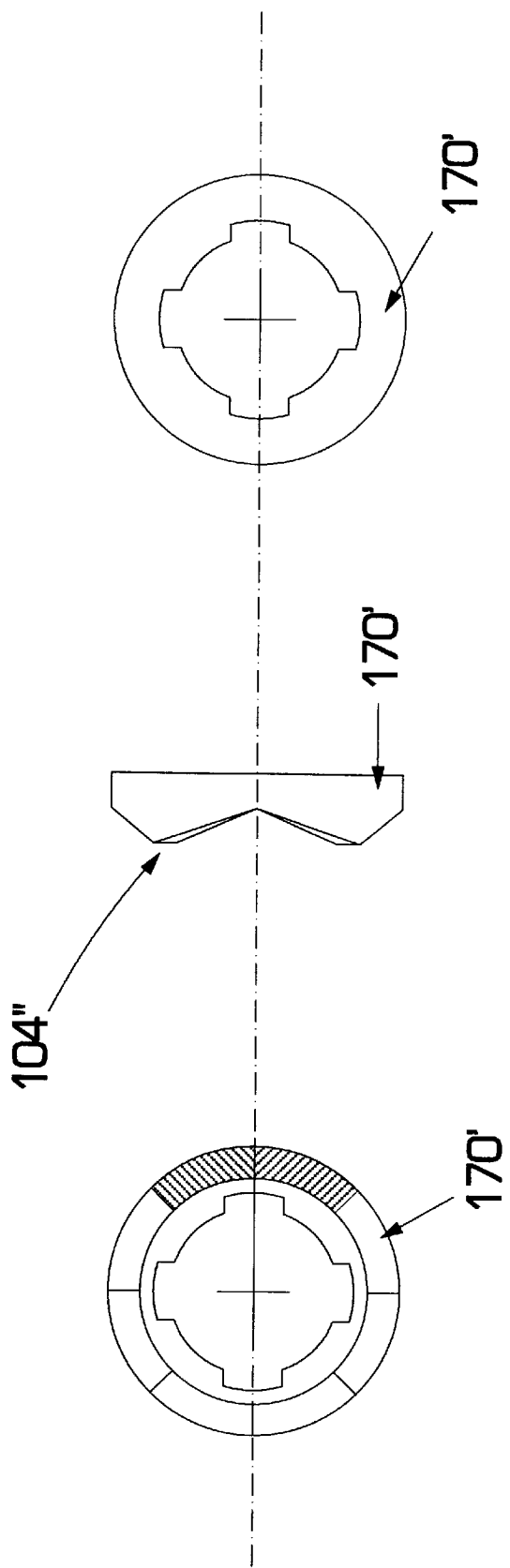
FIGS. 26A–C are various views of a bi-directional ratchet gear in accordance with the embodiment shown in FIG. 14.
Figures 28A, 28B, 28C:
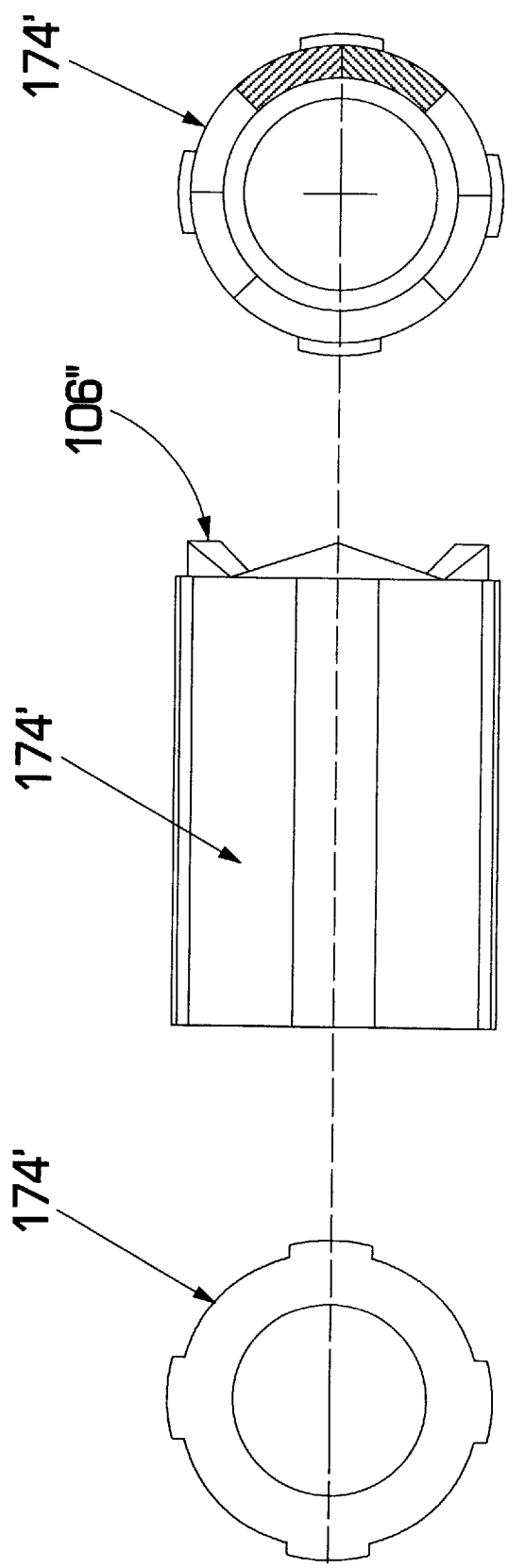
FIGS. 28A–C are various views of a stationary synchronizer in accordance with the embodiment shown in FIG. 14.

As shown in FIGS. 20A and 22A, the rails 1020 extend beyond the radius of the rod 1002. The rails 1020 have a drive engaging portion 1030 that has an exterior surface formed with threads 1032. These threads 1032 are coupled to the corresponding threads on the drive calibrator 168, which is rotated by the actuator knob 112 to set the dosage of the medication to be injected. As shown, the diameter between the threads 1032 on the coupled rails 1020 of the drive portion 176B of the split, two-piece, threaded drive shaft 176 is larger than the diameter or thickness of the rod 1002 with the ratchet teeth 1004, so that the ratchet teeth 1004, which would otherwise interfere with the drive mechanism 120 as the dosage is being set, cannot engage with the drive calibrator 168. Thus, the plunger portion 176A can be retained in the forward position by the ratchet mechanism 1010 engaging the ratchet teeth 1004 of the plunger portion 176A, and the drive portion 176B can be withdrawn and adjusted by the drive calibrator 168 without contacting the ratchet teeth 1004 of the plunger portion 176A.

As shown in FIG. 22A, the engaging portion 1030 of the rails 120 has a larger radius than the rod 1002 and the ratchet teeth 1004. The end cap 180 is fixed (by friction, adhesives or the like) to the splines in the housing 114 to resist rotational movement of the end cap 180. The end cap 180 also includes protrusions 1060 on the interior of the end cap 180 that are shaped to prevent the drive shaft 176 from rotating while adjusting the dosage or depressing the actuator knob 112. In addition, the ratchet mechanism 1010, when contacting the ratchet teeth 1004 of the plunger portion 176A is positioned between the rails 1002 to resist rotation of the drive shaft 176. Thus, in preferred embodiments, the split, two-piece, threaded drive shaft 176 does not rotate and is in a fixed, angular orientation. Therefore, the drive mechanism 120 and the ratchet mechanism 1010 are also maintained in a fixed, angular orientation with respect to the portions 176A and 176B of the split, two-piece, threaded drive shaft.

FIGS. 14–16 show that the drive mechanism 120 uses a round drum 160' (see also FIGS. 7(*c*) and 27A–C) having a plurality of thin bar code lines 102' and thick bar code lines 102" that are read by the counter through an optical sensor 1050 and light pipe 1052. The lines 102' and 102" are grouped in pairs of one thin line 102' next to one thick line 102". The pairs are spaced at predetermined angles around the round drum 160' to represent increments to increase or decrease the dosage amount to be injected. In preferred embodiments, the pairs of lines are spaced at 90° increments around the round drum 160' (although larger or smaller increments may be used). In particular embodiments, the optical sensor 1050 senses one direction of rotation of the round drum 160' by detecting a thin line 102' followed by a thick line 102" and then increments the counter 140 by one for each set of detected lines. Conversely, if the sensor 1050 detects a thick line 102" followed by a thin line 102', it determines that the rotation is in the opposite direction and decrements the counter 140 by one. In alternative embodiments, the lines may be a reflective material, rather than dark bar code lines. In further alternatives, the sensor 1050 may use infrared (IR) radiation or may use optical sensors that do not require light pipes 1052.

FIGS. 14–16, 26A–C and 28A–C illustrate that the drive mechanism uses a bi-directional ratchet gear 170' and a corresponding bi-directional stationary synchronizer 174' having teeth 104" and 106", respectively. The shape of the teeth 104" and 106" are symmetrical, as opposed to the right angular teeth 104 and 106 on the gear 70 and synchronizer 74 (see FIG. 7(*a*)), to permit the dosage set by the counter 140 and displayed on the display 134 to be increased and decreased. Thus, users can correct the set dosage if they go past the desired dosage amount, without having to reset the pen or ejecting the incorrectly set dosage.

To set up the drive mechanism 120 with a new medication cartridge 122, a user depresses the start button 138 and retracts the drive mechanism 120 to its rearmost position by rotating the actuator knob 112. Then the user screws a medication cartridge 122 onto the injection housing 114, until it contacts and moves the medication cartridge tensioner and synchronizer 182 back towards the actuator knob 112. This forces the integral legs 182 of the medication cartridge synchronizer and tensioner 182 to pass through the end cap 80 (which is plastic welded or bonded to the housing 114) to press the wedge cap 1014 into contact the ratchet mechanism 1010, which in turn forces the ratchet mechanism 1010 down to engage the ratchet teeth 1004 of the plunger portion 176A of the split, two-piece, threaded drive shaft 176. Thus, once the medication cartridge 122 is attached to the housing 114, the plunger portion 176A can only move forward towards the piston 184 of the medication cartridge 122.

To give an injection, the user depresses the start button 138. This releases the actuator knob 112 and moves the drive mechanism 120, along with the drive calibrator 168, back a fixed distance X. As the drive calibrator 168 moves back, it also pulls back the drive portion 176B of the split, two-piece, threaded drive shaft 176 a distance X, since it is directly coupled by the threads 1032 to the corresponding threads on the drive calibrator 168. However, the plunger portion 176A remains in position, because the ratchet mechanism 1010 and ratchet teeth 1004 inhibit rearward movement. Also, the connectors 1023 and 1024 joining the rails 1020 together move freely back a distance X through the aperture 1008 in the rod 1002 without bearing against the end of the aperture 1008 towards the actuator knob 112. In preferred embodiments, the length of the aperture 1008 exactly corresponds to the distance X to prevent negative dosages from being set. However, in alternative embodiments, longer lengths may be used, since contact at the rear of the aperture 1008 is not required if alternative techniques for preventing negative dosages from being set are used.

Once the drive mechanism 120 is moved back the distance X, the user rotates the actuator knob 112 to move the rails 1020 of the drive portion 176B by a distance Y to decrease the distance between the end 1026 of the aperture 1008 and the connectors 1023 and 1024 to a distance that is less than X (i.e., X−Y<X). This reduction in distance corresponds to the amount of medication to be injected. If no rotation of the actuator knob occurs (i.e., Y=0 and X−Y=X) and the user just depresses the actuator knob 112, no medication will be delivered since the connectors 1023 and 1024 will return to their original position and will not move the plunger portion 176A forward. If the distance between the end 1026 of the aperture 1008 and the connectors 1023 and 1024 is reduced by Y to a value less then X (i.e., X−Y<X), the connectors 1023 and 1024 will end up at a position than is farther forward than their original position prior to activating the drive mechanism. If the distance between the end 1026 of the aperture 1008 and the connectors 1023 and 1024 is reduced to zero (i.e., Y=X and X−Y=0), the connectors 1023 and 1024 will end up at a position that is farther forward by X than their original position prior to activating the drive mechanism and the maximum dosage corresponding to the distance X will be set. Thus, once the user depresses the actuator knob 112, the connectors 1023 and 1024 will contact and force the end 1026 of the aperture 1008 forward a corresponding amount Y that equals the distance required to deliver the set dosage.

Since, as discussed above, the drive mechanism is bi-directional, the user can adjust the dosage both ways to correct for over rotation of the actuator knob 112. However, in preferred embodiments, the user cannot rotate to a value of less than 0 units when a medication cartridge 122 is attached to the injection housing 114. For example, the drive calibrator 168 and dosage knob drive shaft 152 only move back a distance until they contact a wall 1062.

After the user has set the dosage, the user depresses the actuator knob 112 once, until the start button 138 re-engages the drive mechanism 120. This moves the drive mechanism 120, along with the drive calibrator 168, forward the distance X toward the medication cartridge 122. At the same time, the drive portion 176B of the split, two-piece, threaded drive shaft 176 is also moved forward the distance X toward the medication cartridge 122. As the drive portion 176B moves forward, the connectors 1023 and 1024 ultimately contact and bear against the end 1026 of the aperture 1008 of the plunger portion 176A. This forces the plunger portion 176A to move forward a distance Y corresponding to the dosage set (i.e., equal to the reduction in the distance X between the end 1026 of the aperture 1008 and the connectors 1023 and 1024), while the drive portion 176B moves the distance X. The depression of the actuator knob 112 moves the plunger portion 176A forward past the ratchet mechanism 1010, which then engages the next tooth of the ratchet teeth 1004 to inhibit the rearward movement of the plunger portion 176A after each increment of forward movement during the injection. Thus, the user can easily set and administer the injection by depressing a button, rotating a knob, and then depressing the knob, without withdrawing the plunger 178 of the plunger portion 176A from the piston 184 of the medication cartridge 122. Also, the user is not required to use a complicated procedure to engage and disengage the drive mechanism 120 from the split, two-piece, threaded drive shaft 176, since the drive mechanism 120 is always engaged with the drive portion 176A.

The illustrated direct drive mechanism only requires a single complete depression of the actuator knob 112 to inject different set amounts of medication. The illustrated direct drive allows the user to accurately set various dosage values to be injected. The drive mechanism 120 is capable of providing dosage accuracies of between 0.1 to 1.0-unit increments. However, other dosage increments may be used.

FIGS. 20B and 22B illustrate an alternative embodiment, which uses modified rails 1020' that wrap around the rod 1002 to provide greater rigidity and resistance to bending and flexing under the hydraulic loads experienced during administration of an injection. The wrap around arrangement engagement portions 1030' of the rails 1020' leave open a ratchet channel 1034. The ratchet channel 1034 permits the drive portion 176B to still slide past the ratchet mechanism 1010, which engages the ratchet teeth 1004 of the rod 1002 that are set within the ratchet channel 1034.

In preferred embodiments, the drive shaft 176A and 176B are formed from metal and many of the other components in the drive mechanism are formed from plastic. However, in alternative embodiments, the drive shaft 176A and 176B and the various components of the drive mechanisms may be formed from metal, ceramics, plastics, composites or a combination of materials.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A medication injection mechanism for delivering a dosage of medication from a medication cartridge having a piston, the injection mechanism comprising:

a two-piece drive shaft including:

a plunger portion having an end that can contact the piston of the medication cartridge, the plunger portion also having ratchet receiving means disposed on sides of the plunger portion that define a thickness of the plunger portion, the plunger portion further including an opening to provide a passage through the plunger portion of the two-piece drive shaft; and a drive portion formed by members coupled together through the opening in the plunger portion so that the drive portion is coupled to the plunger portion and the drive portion can move relative to the plunger portion, wherein each of the members has threads on a surface that extends beyond the defined thickness of the plunger portion;

a ratchet mechanism that engages with the ratchet receiving means of the plunger portion to permit movement toward the piston of the medication cartridge and to inhibit movement of the plunger portion away from the piston of the medication cartridge; and a drive mechanism that engages the threads on the drive portion and which is also free of contact with the ratchet receiving means to adjust the position of the drive portion relative to the plunger portion so that the drive portion can be moved toward the piston of the medication cartridge a fixed distance and the plunger portion is moved a distance that is less than or equal to the fixed distance.

2. A medication injection mechanism in accordance with claim 1, wherein the defined thickness of the plunger portion is equal to a diameter of the plunger portion.

3. A medication injection mechanism in accordance with claim 1, wherein the threads of the drive mechanism are engaged with the threads of the drive portion of the drive shaft while setting the dosage of medication, injecting and delivering the dosage, and after injecting and delivering the dosage of medication.

4. A medication injection mechanism in accordance with claim 1, further comprising:
 a safety release coupled to the drive mechanism to secure the drive mechanism in place after delivery of the dosage of medication; and
 an actuator coupled to the drive mechanism for setting the dosage of medication and for actuating the drive mechanism to deliver the dosage of medication.

5. A medication injector mechanism in accordance with claim 4, wherein the threads of the drive mechanism are engaged with the threads of the drive portion of the drive shaft while setting the dosage of medication, injecting and delivering the dosage, and after injecting and delivering the dosage of medication, and wherein the dosage of medication is set and delivered by releasing the safety release, adjusting the actuator and activating the actuator.

6. A medication injection mechanism for delivering a dosage of medication from a medication cartridge having a piston, the injection mechanism comprising:
 a two-piece drive shaft including:
  a plunger portion having an end that can contact the piston of the medication cartridge, the plunger portion also having ratchet members disposed on opposite sides of the plunger portion to define a thickness of the plunger portion and a pair of track slots oriented on two other opposite sides of the plunger portion, the plunger portion further including an opening to provide a passage between the track slots; and
  a drive portion formed by a pair of rails disposed within the pair of track slots of the plunger portion and coupled together by a connector passing through the opening in the plunger portion so that the drive portion is coupled to the plunger portion and the drive portion can move relative to the plunger portion, wherein each of the rails has threads on a surface that extends beyond the track slots and the defined thickness of the plunger portion;
 a ratchet mechanism that engages with the ratchet members of the plunger portion to permit movement toward the piston of the medication cartridge and to inhibit movement of the plunger portion away from the piston of the medication cartridge; and
 a drive mechanism that engages the threads on the drive portion and which is also free of contact with the ratchet members to adjust the position of the drive portion relative to the plunger portion so that the drive portion can be moved toward the piston of the medication cartridge a fixed distance and the plunger portion is moved a distance that is less than or equal to the fixed distance.

7. A medication injection mechanism in accordance with claim 6, wherein the defined thickness of the plunger portion is equal to a diameter of the plunger portion.

8. A medication injection mechanism in accordance with claim 6, wherein the threads of the drive mechanism are engaged with the threads of the drive portion of the drive shaft while setting the dosage of medication, injecting and delivering the dosage, and after injecting and delivering the dosage of medication.

9. A medication injection mechanism in accordance with claim 6, further comprising:
 a safety release coupled to the drive mechanism to secure the drive mechanism in place after delivery of the dosage of medication; and
 an actuator coupled to the drive mechanism for setting the dosage of medication and for actuating the drive mechanism to deliver the dosage of medication.

10. A medication injector mechanism in accordance with claim 9, wherein the threads of the drive mechanism are engaged with the threads of the drive portion of the drive shaft while setting the dosage of medication, injecting and delivering the dosage, and after injecting and delivering the dosage of medication, and wherein the dosage of medication is set and delivered by releasing the safety release, adjusting the actuator and activating the actuator.

11. A medication injection mechanism for delivering a dosage of medication from a medication cartridge having a piston, the injection mechanism comprising:
 a two-piece drive shaft including:
  a plunger portion having an end that can contact the piston of the medication cartridge, the plunger portion also having ratchet teeth disposed on at least two sides of the plunger portion and at least two track slots oriented on at least two other sides of the plunger portion, the plunger portion further including an aperture to provide a passage between the track slots; and
  a drive portion formed by at least two rails disposed within the at least two track slots of the plunger portion and coupled together through the opening in the plunger portion so that the drive portion is coupled to the plunger portion and the drive portion can move relative to the plunger portion, wherein each of the rails has threads on a surface that extends beyond the track slots of the plunger portion;
 a ratchet mechanism that engages with the ratchet teeth of the plunger portion to permit movement toward the piston of the medication cartridge and to inhibit movement of the plunger portion away from the piston of the medication cartridge; and
 a drive mechanism that engages the threads on the drive portion and which is also free of contact with the ratchet teeth to adjust the position of the drive portion relative to the plunger portion so that the drive portion can be moved toward the piston of the medication cartridge a fixed distance and the plunger portion is moved a distance that is less than or equal to the fixed distance.

12. A medication injection mechanism in accordance with claim 11, wherein the threads of the drive mechanism are engaged with the threads of the drive portion of the drive shaft while setting the dosage of medication, injecting and delivering the dosage, and after injecting and delivering the dosage of medication.

13. A medication injection mechanism in accordance with claim 11, further comprising:

a safety release coupled to the drive mechanism to secure the drive mechanism in place after delivery of the dosage of medication; and an actuator coupled to the drive mechanism for setting the dosage of medication and for actuating the drive mechanism to deliver the dosage of medication.

14. A medication injector mechanism in accordance with claim 13, wherein the threads of the drive mechanism are engaged with the threads of the drive portion of the drive shaft while setting the dosage of medication, injecting and delivering the dosage, and after injecting and delivering the dosage of medication, and wherein the dosage of medication is set and delivered by releasing the safety release, adjusting the actuator and activating the actuator.

* * * * *